United States Patent [19]

Montgomery et al.

[11] Patent Number: 5,591,722

[45] Date of Patent: Jan. 7, 1997

[54] 2'-DEOXY-4'-THIORIBONUCLEOSIDES AND THEIR ANTIVIRAL ACTIVITY

[75] Inventors: John A. Montgomery; John A. Secrist, III, both of Birmingham, Ala.

[73] Assignee: Southern Research Institute, Birmingham, Ala.

[21] Appl. No.: 354,313

[22] Filed: Dec. 12, 1994

Related U.S. Application Data

[63] Continuation of Ser. No. 35,689, Mar. 23, 1993, abandoned, which is a continuation-in-part of Ser. No. 408,040, Sep. 15, 1989, abandoned.

[51] Int. Cl.$^6$ .......................... A61K 31/70; C07H 17/02; C07H 5/10; C07D 327/04

[52] U.S. Cl. .................. 514/45; 514/46; 514/49; 514/50; 536/4.1; 536/27.1; 536/27.13; 536/27.21; 536/27.6; 536/27.61; 536/27.63; 536/27.7; 536/27.81; 536/28.1; 536/28.5; 536/28.52; 536/28.53; 536/28.54; 536/28.55; 549/30; 549/31; 549/33

[58] Field of Search .................. 536/4.1, 27.1, 536/27.13, 27.21, 27.6, 27.61, 27.63, 27.7, 27.81, 28.1, 28.5, 28.52, 28.53, 28.54, 28.55; 549/30, 31, 33; 514/45, 46, 49, 50

[56] References Cited

U.S. PATENT DOCUMENTS

| | | | |
|---|---|---|---|
| 4,645,756 | 2/1987 | Hill et al. | 514/24 |
| 4,698,422 | 10/1987 | Hill et al. | 536/17.1 |
| 4,820,692 | 4/1989 | Riscoe et al. | 514/23 |
| 4,902,675 | 2/1990 | Hill et al. | 514/24 |
| 5,128,458 | 7/1992 | Montgomery et al. | 536/4.1 |
| 5,180,714 | 1/1993 | Sufrin et al. | 514/46 |

FOREIGN PATENT DOCUMENTS

| | | |
|---|---|---|
| 0514036 | 11/1992 | European Pat. Off. . |
| 8808001 | 10/1988 | WIPO . |
| 9116333 | 10/1991 | WIPO . |
| 9206993 | 4/1992 | WIPO . |

OTHER PUBLICATIONS

Dyson et al. (I), "The Synthesis and Antiviral Activity of Some 4'-Thio-2'-deoxynucleoside Analogs," *Nucleic Acids Res. Symps. Ser., No. 24,* IRL Press, Oxford, UK, pp. 1–4. Chem. Abstr., 117(21), p. 31, Abstr. No. 204617a (1992).
Dyson et al. (II), "The Synthesis and Antiviral Properties of E-5-(2-bromovinyl)-4'-thio-2'-deoxyuridine," *J. Chem. Soc., Chem. Comm.,* (11), 741–742 (1991).
Dyson et al. (III), "The Synthesis and Antiviral Activity of Some 4'-Thio-2'-deoxy Nucleoside Analogues," *J. Med. Chem.,* 34, 2782-27–86 (1991).
Secrist et al., "Synthesis and Anti–HIV Activity of 4'-Thio-2',3'-dideoxynucleosides," *J. Med. Chem.,* 35, 533–538 (1992).
Adley et al., "Thio–Sugars. Part I. The Thiofuranose Ring," *J. Chem. Soc.,* 1966 (Sec. C), 1287–1290.
Owen et al., "Thio–Sugars. Part II. The Thiofuranose Ring," *J. Chem. Soc.,* 1966 (Sec. C), 1291–1296.
Clayton et al., "Derivatives of D–Ribothiafuranose," *Chem. & Ind.,* 1962, 1795–1796.
Miura et al., "4'-Thioadenosine as a Novel Inhibitor of S–Adenosylhomocysteine Hydrolase and an Inducer for the Differentiation of HL–60 Human Leukemia Cells," in *Purine and Pyimidine Metabolism V. Part B,* Nyhan et al. eds., Plenum Publ Co., 1986, pp. 667+?.
Ritchie et al., "Addition of Pseudohalogens to Unsaturated Carbohydrates. VI Synthesis of 4'-Thiacordycepin," *Can. J. Chem.,* 56, 794–802 (1978).
Reist et al., "Thio Sugars. Synthesis of the Adenine Nucleosides of 4–Thio–D–xylose and 4–Thio–D–arabinose," *J. Org. Chem.,* 33(1), 189–192 (1968).
Ototani et al., "Preparation and Antitumor Activity of 4'-Thio Analogs of 2,2'-Anhydro–1–β–arabinofuranosylcytosine," *J. Med. Chem.,* 17(5), 535–537 (1974).
Fu et al.(I), "An Alternative Synthesis of Anomeric Methyl 2–Deoxy–4–thia–D–erythro–pentofuranosides," *J. Org. Chem.,* 41(24), 3831–3834 (1976).
Whistler et al., "Anomeric Methyl 4–Thio–D–arabinosylfuranosides," *J. Org. Chem.,* 35(2), 519–521 (1970).
Fu et al. (II), "The Trimethylsilyl Synthesis of 2'-Deoxy–4–thionucleosides in the Presence of Mercuric Bromide and Mercuric Oxide," in *Nucleic Acid Chemistry/Improved & New Synthetic Procedures, Methods & Techniques, Part One,* Townsend & Tipson(eds), John Wiley & Sons, Inc., New York, NY, 1978, pp. 317–323 only.
Hanessian et al., "Stereochemical Control of Nature's Biosynthetic Pathways: A General Strategy for the Synthesis of Polypropionate–Derived Structural Units for a Single Chiral Progenitor," *Tetrahedron,* 43(21), 5505–5572 (1987).

Primary Examiner—John Kight
Assistant Examiner—L. Eric Crane
Attorney, Agent, or Firm—Yahwak & Associates

[57] ABSTRACT

2'-Deoxy-4'-thio-ribonucleosides, intermediates in their production, and their use as antiviral and anticancer agents are disclosed.

21 Claims, No Drawings

2'-DEOXY-4'-THIORIBONUCLEOSIDES AND THEIR ANTIVIRAL ACTIVITY

CROSS-REFERENCE TO RELATED APPLICATION

This application is a continuation of Ser. No. 08/035,689, filed Mar. 23, 1993 now abandoned, which is a continuation-in-part of application Ser. No. 07/408,040, filed Sep. 15, 1989, now abandoned.

BACKGROUND OF THE INVENTION

1. Field of the Invention

This invention relates to 2'-deoxy-4'-thioribonucleosides and intermediates useful in their production, and to the use of 2'-deoxy-4'-thioribonucleosides as antiviral and anticancer agents.

A nucleoside is a molecule comprised of a pentose sugar in a furanose ring joined to a nitrogenous heterocyclic base that is a derivative of either purine or pyrimidine. A 4'-thionucleoside is a nucleoside wherein the furanose ring oxygen has been replaced by sulfur. A 2'-deoxy-4'-thioribonucleoside is a 4'-thionucleoside wherein the pentose sugar is 2'-deoxy-D-ribose.

As used herein, the terms "nucleoside", "4'-thionucleoside" and "2'-deoxy-4'-thioribonucleoside" shall also include compounds wherein the nitrogenous heterocyclic base is a base related to the purine and pyrimidine bases, but with a ring alteration, such nitrogenous heterocyclic bases including 3-deazapurines, 7-deazapurines, 8-azapurines, 2-azapurines, 5-azapyrimidines, 6-azapyrimidines, and 3-deazapyrimidines and shall also include compounds having acyl protecting groups at the 3' position, or the 5' position, or both, of the 2'-deoxy-D-ribose.

2. Description of the Related Art

Several 4'-thionucleosides have been reported in the literature. Reist, et al, *J. Am. Chem. Soc.*, 86, 5658 (1964) disclose L and D forms of 4'-thioriboadenosine. Biological effects of 4'-thioriboadenosine are described in Miura, et al in *Purine and Pyrimidine Metabolism in Man, V, Part B*, (Plenum Publishing Corp., 1986) p. 667. Richie, et al, *Can. J. Chem.*, 56, 794 (1977) disclose the synthesis of 9-(3-deoxy-4-thio-β-D-erythro-pentofuranosyl)adenine (4'-thio-cordycepin). Reist, et al, *J. Org. Chem.*, 33, 189 (1968) describe the synthesis of adenine nucleosides of 4-thio-D-xylose and 4-thio-D-arabinose. Ototani, et al. *J. Med. Chem.*, 17, 535 (1974) disclose the preparation and antitumor activity of 4'-thio-1-β-D-arabinofuranosylcytosine and 2,2'-anhydro-4'-thio-1-β-D-arabinofuranosylcytosine hydrochloride.

The description, preparation and use of specific 2'-deoxy-4'-thioribonucleosides is not found in the literature. Fu, et al, *J. Org. Chem.*, 41, 3831 (1976) disclose a method for the preparation of anomeric methyl-2-deoxy-4-thio-D-erythro-pentofuranosides and suggest that the furanosides could be used as precursors for the synthesis of 2'-deoxy-4'-thionucleosides.

SUMMARY OF THE INVENTION

It has now been found that certain 2'-deoxy-4'-thioribonucleosides have useful antiviral and anticancer activities. Thus, in accordance with this invention, there are provided novel 2'-deoxy-4'-thioribonucleosides represented by the formula

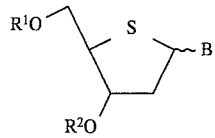

wherein:

B indicates that B can be either alpha or beta, and

B is a nitrogenous heterocyclic base selected from the group consisting of pyrimidine, 5-azapyrimidine, 6-azapyrimidine, 3-deazapyrimidine, purine, 3-deazapurine, 7-deazapurine, 8-azapurine, and 2-azapurine bases. By the term "pyrimidine base" is meant any pyrimidine derivative including, but not limited to, uracil (2,4-dioxopyrimidine), thymine (5-methyl-2,4-dioxopyrimidine), cytosine (4-amino-2-oxopyrimidine), and 5-methylcytosine (4-amino-5-methyl-2-oxopyrimidine), and derivatives having a halogen attached to the $C^5$ heterocyclic carbon By the term "5-azapyrimidine base" is meant any 5-azapyrimidine derivative including, but not limited to, 5-aza-2,4-dioxopyrimidine and 4-amino-5-aza-2-oxopyrimidine. By the term "6-azapyrimidine base" is meant any 6-azapyrimidine derivative including, but not limited to, 6-aza-2,4-dioxopyrimidine, 4-amino-6-aza-2-oxopyrimidine, and derivatives having a methyl group or halogen attached to the $C^5$ heterocyclic carbon. By the term "3-deazapyrimidine base" is meant any 3-deazapyrimidine derivative including, but not limited to, 3-deaza-2,4-dioxopyrimidine, 4-amino-3-deaza-2-oxopyrimidine, and derivatives having a methyl group or halogen attached to the $C^5$ heterocyclic carbon. By the term "purine base" is meant any purine derivative including, but not limited to, adenine (6-aminopurine), guanine (2-amino-6-oxopurine), 2,6-diaminopurine, 1-6-dihydro-6-oxopurine, and derivatives having a halogen attached to the $C^2$ heterocyclic carbon. By the term "3-deazapurine base" is meant any 3-deazapurine derivative including, but not limited to, 6-amino-3-deazapurine, 3-deaza-6-oxopurine, and derivatives having an amino group or halogen attached to the $C^2$ heterocyclic carbon. By the term "7-deazapurine base" is meant any 7-deazapurine derivative including, but not limited to, 6-amino-7-deazapurine, 7-deaza-6-oxopurine, and derivatives having an amino group or a halogen attached to the $C^2$ heterocyclic carbon. By the term "8-azapurine base" is meant any 8-azapurine derivative including, but not limited to, 6-amino-8-azapurine, 8-aza-6-oxopurine, and derivatives having a halogen attached to the $C^2$ heterocyclic carbon. By the term "2-azapurine base" is meant any 2-azapurine derivative including, but not limited to, 6-amino-2-azapurine and 2-aza-6-oxopurine. $R^1$ and $R^2$ in the above diagram may be the same or different and may be hydrogens or conventional acyl protecting groups. For a range of the protecting groups $R^1$ and $R^2$ that can be used, see T. W. Greene, "Protecting Groups in Organic Synthesis", 1981, John Wiley, New York, the disclosure of which is incorporated herein by reference.

The invention may be illustrated by the following, wherein the compounds encompassed by the invention are represented by the formula

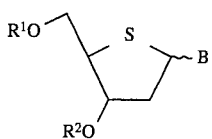

wherein:

B indicates that B can be either alpha or beta, and

B is a member selected from the group consisting of the following nitrogenous heterocyclic bases:

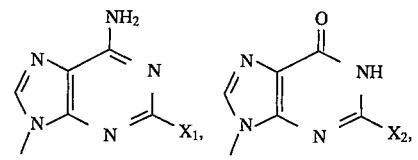

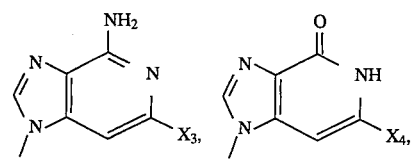

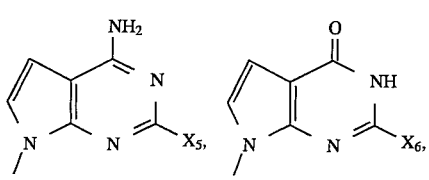

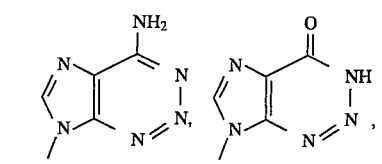

where $X_1, X_2, X_3, X_4, X_5, X_6, X_7, X_8$=H, $NH_2$ or halogen,

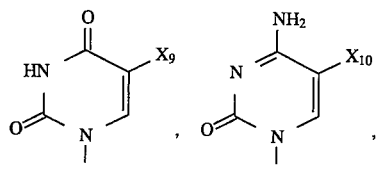

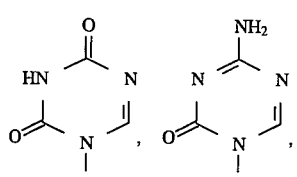

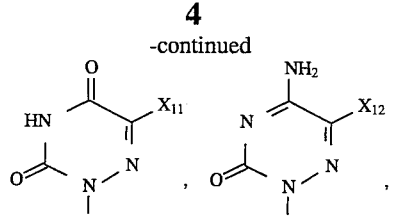

where $X_9, X_{10}, X_{11}, X_{12}, X_{13}, X_{14}$=H, $CH_3$, or halogen and $R^1$ and $R^2$ can be the same or different and may be hydrogen or acyl protecting groups.

Preferably, the nitrogenous heterocyclic base is selected from the group consisting of the following purine and pyrimidine bases:

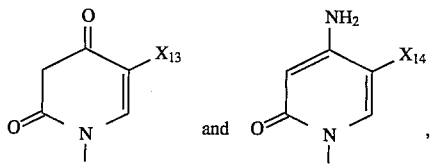

where $X_{15}, X_{16}$=H, $NH_2$ or halogen, and

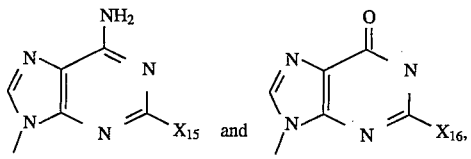

where $X_{17}, X_{18}$=H, $CH_3$ or halogen.

According to another aspect of this invention, there is administered to a host animal, including man, afflicted with a viral infection, e.g., an infection caused by herpes, simplex virus types 1 or 2, a therapeutically effective amount of a 2'-deoxy-4'-thioribonucleoside as previously defined.

According to another aspect of this invention, there is administered to a host animal, including man, afflicted with cancer, a therapeutically effective amount of a 2'-deoxy-4'-thioribonucleoside as previously defined. By the term "cancer" is meant any new and abnormal cell growth, specifically a new growth of tissue which is uncontrolled and progressive. Compounds of this invention may be used, for example, in the treatment of leukemias, epidermoid carcinoma, lymphomas, choriocarcinoma, Wilm's tumor, neuroblastoma, rhabdomyosarcoma, carcinoma of the testis, and breast and lung tumors.

In accordance with still another aspect of this invention, there are provided novel intermediates useful in the preparation of certain 2'-deoxy-4'-thioribonucleosides.

DETAILED DESCRIPTION OF THE INVENTION

The synthesis of the 2'-deoxy-4'-thioribonucleosides may be carried out by beginning with 1-O-methyl 2'-deoxy-4-thio-α,β-D-ribofuranose of formula 1

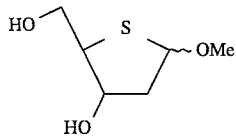

the preparation of which is described in Fu, et al, *J. Org. Chem.*, 41, 3831 (1976), the disclosure of which is incorporated herein by reference. The compound of formula 1 is reacted with p-toluoyl chloride to give the compound of formula 2

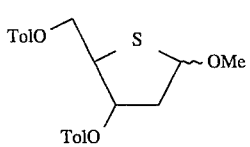

The methyl group is then replaced by an acetyl group to give the compound of formula 3

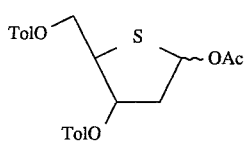

The 2'-deoxy-4'-thioribonucleosides are prepared by coupling compound 3 with nitrogenous heterocyclic bases and then removing the toluoyl protecting groups. Compound 3 is coupled with a purine in the presence of tin(IV) chloride. (See Saneyoshi, et al, *Chem. Pharm. Bull.*, 27, 2518 (1979), the disclosure of which is incorporated herein by reference). Compound 3 is coupled with a 3-deazapurine, 7-deazapurine, 8-azapurine or 2-azapurine in a similar manner. Compound 3 is coupled with a pyrimidine using the catalysts hexamethyldisilazane, trimethylchlorosilane, and trimethylsilyl trifluoromethanesulfonate (see Vorbruggen, et al, *Chem. Ber.*, 114, 1234 (1981), the disclosure of which is incorporated herein by reference). Compound 3 is coupled with a 5-azapyrimidine, 6-azapyrimidine and 3-deazapyrimidine in a similar manner. The coupling reaction provides both α and β nucleosides in most cases. Anomers may be separated by conventional methods.

As examples of the preparation of purine compounds of this invention, compound 3 can be reacted with 2,6 dichloropurine in the presence of tin(IV) chloride to give the compound of formula 4

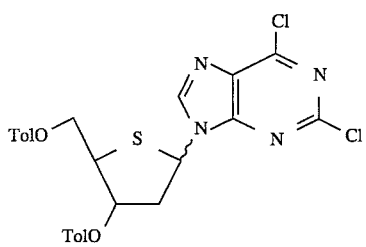

Compound 4 can be reacted with saturated ethanolic $NH_3$ to give the compound of formula 5

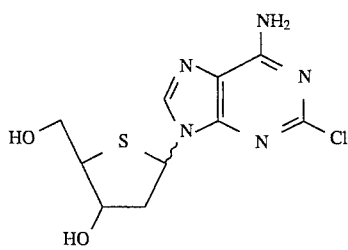

Compound 4 can also be reacted with sodium azide to give the compound

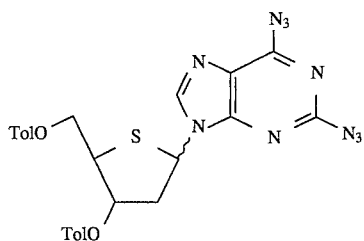

which can be reduced to the compound of formula 7:

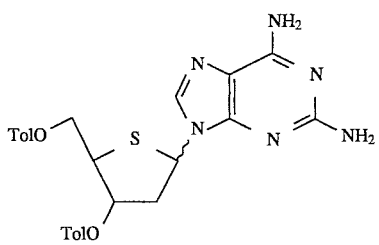

Deprotection of compound 7 gives the compound of formula 8

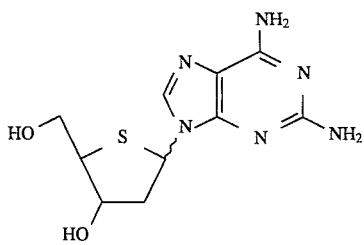

Compound 8 can be reduced to the compound of formula 9

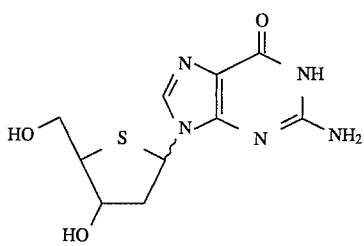

Compound 3 can also be reacted with 2-fluoroadenine in the presence of tin(IV) chloride to give the compound of formula 10

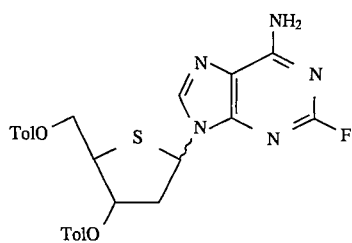

Removal of the toluoyl protecting groups gives the compound of formula 11

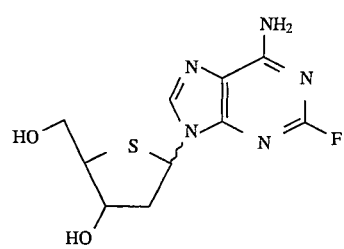

Compound 3 can also be reacted with 6-chloropurine in the presence of tin(IV) chloride to give the compound of formula 12

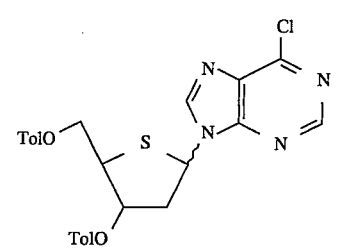

Reaction with saturated ethanolic NH$_3$ gives the compound of formula 13

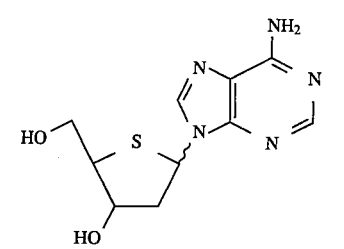

Compound 13 can be reduced to the compound of formula 14

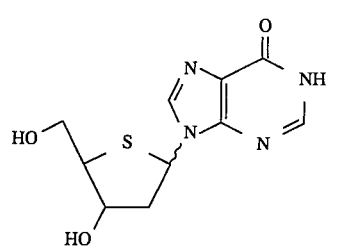

As examples off the preparation of pyrimidine compounds of this invention, the compound of formula 3 can be combined with uracil to give the compound of formula 15 (β:α ratio appr. 1:1)

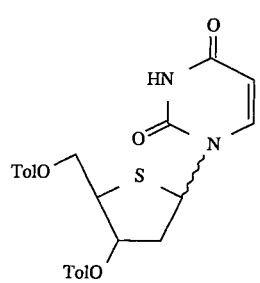

fractional crystallization of 15 affords pure anomers α-15 and β-15.

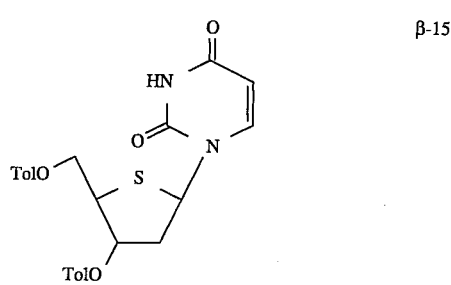

Removal of the toluoyl protecting groups gives the compounds of the formula α-16 and β-16

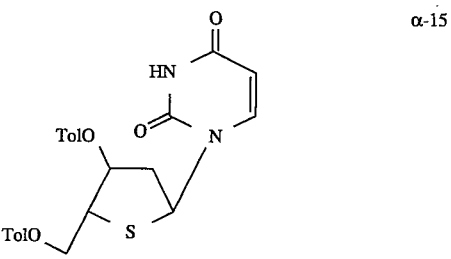

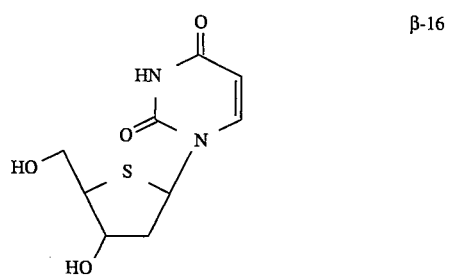

The compound of formula 3 can also be combined with thymine to give the compound of formula 17 (β:α ratio appr. 1:1)

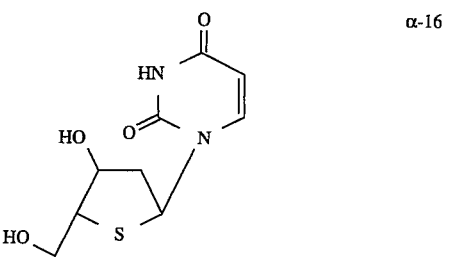

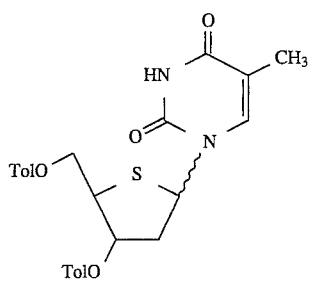

17 fractional crystallization of 17 affords pure anomers α-17 and β-17

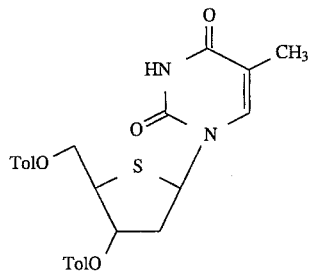

β-17

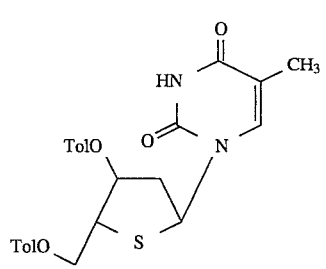

α-17

Removal of the toluoyl protecting groups gives the β-17 compounds of formula α-18 and β-18

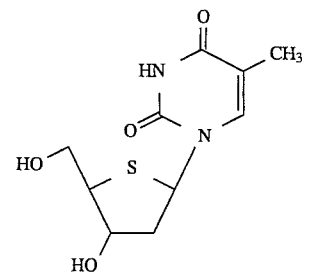

β-18

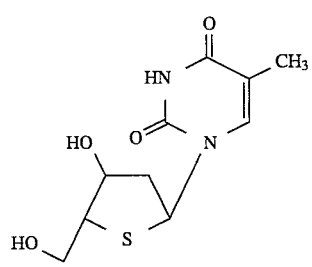

α-18

The compound of formula 3 can also be combined with cytosine to give the compound of formula 19 (β:α ratio appr. 1:1)

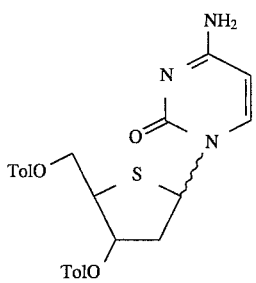

19

Removal of the toluoyl protecting groups gives the compounds of the formula 20

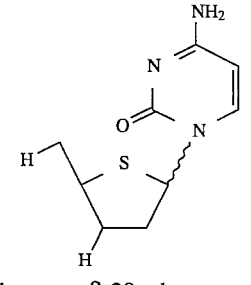

20

To obtain the pure β-20, the compound β-20 can be treated with 1,2,4 triazole and p-chlorophenyl phosphodichlorodate in pyridine to give the intermediate 21

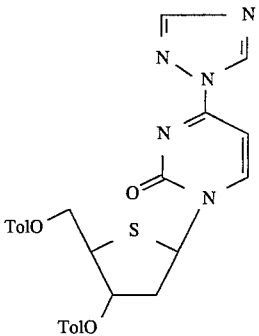

21 which can be converted directly to the compound β-20 by sequential treatment with ammonium hydroxide and sodium methoxide.

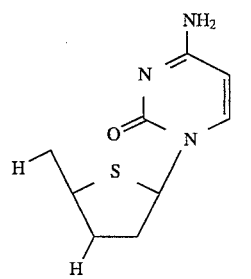

β-20

In carrying out the synthesis of 2'-deoxy-4'-thioribonucleosides of this invention, other acyl protecting groups besides the toluoyl protecting group may be used. Further, conventional acyl protecting groups may be substituted or added, using conventional methods, to the 3' position or 5' position, or both, of the 2'-deoxy-4-thioribonucleosides.

The antiviral activity and cytotoxicity of 2'-deoxy-4'-thioribonucleosides of the present invention may be readily determined according to the methods set forth in J. A. Secrist, A. T. Shortnacy, and J. A. Montgomery, *J. Med. Chem.* 1988 31, 405, the disclosure of which is incorporated herein be reference, or by any other methods known in the art.

The 2'-deoxy-4'-thioribonucleosides may be used in the treatment of various human and animal diseases caused by viruses, such as herpes simplex virus and human cytomegalovirus and in the treatment of various cancers, including leukemia L1210, human T-cell leukemia CCRF-CEM, and human epidermoid carcinoma no. 2. Determination of the antiviral activity and cytotoxicity of a particular 2'-deoxy-4'-thioribonucleoside and determination of the optimum method of administration and optimum dosage in the treatment of a vital infect[on or cancer is within the skill of the art.

The following examples illustrate the preparation of the compounds described above. In these examples, MeOH is methyl alcohol, EtOH is ethyl alcohol, and $Me_2SO$-$d_6$ is deuterated dimethyl sulfoxide $(CD_3)_2SO$.

All evaporations were carried out in vacuo with a rotary evaporator or by short path distillation into a dry ice-acetone cooled receiver under high vacuum. Analytical samples were normally dried in vacuo over $P_2O_5$ at room temperature for 16 hours. Analtech precoated (250 μm) silica gel G(F) plates were used for TLC analyses; the spots were detected by irradiation with a mineral light and/or by charring after spraying with saturated $(NH_4)_2SO_4$. All analytical samples were TLC homogeneous. Melting points were determined with a Mel Temp capillary melting point apparatus unless otherwise specified. Purifications by flash chromatography were carried out on Merck silica gel 60 (230–400 mesh) using the slurry method of column packing. The uv absorption spectra were determined in 0.1N HCl (pH 1), pH 7 buffer, and 0.1N NaOH (pH 13) with a Cary 17 spectrophotometer; the maxima are reported in nanometers ($E\times10^{-3}M^{-1}$, $CM^{-1}$). The NMR spectra in $Me_2SO$-$d_6$ or $CDCl_3$ with tetramethylsilane as an internal reference were determined with a Nicolet NT 300NB Spectrometer operating at 300–635 MHz. Chemical Shifts ($\delta$) quoted in the case of multiplets were measured from the approximate center. Where necessary, the chemical shift and coupling constant values for the non-first order parts of the spectra were obtained from simulated spectra by employing the General Electric/Nicolet ITRACAL program for iterative analysis. The mass spectral data were obtained with a Varian-MAT 311A mass spectrometer in the fast atom bombardment mode. Where analysis are indicated only by symbols of the elements, analytical results obtained for those elements were within ±0.4% of the theoretical values.

EXAMPLE 1

1-O-Acetyl-2-deoxy-4-thio-3,5-di-O-p-toluoyl-α,β-D-ribofuranose (formula 3)

To a solution of 1-O-methyl-2-deoxy-4-thio-α,β-D-ribofuranose (formula 1) (10 g, 60.97 mmol) in 250 mL of sieve-dried pyridine was added p-toluoyl chloride (23.57 g, 152.5 mmol) dropwise at 0°–5° C. The cooling bath was removed. After the reaction stirred for 10 hours, the reaction was essentially complete as indicated by TLC ($CHCl_3$-MeOH 10:1). The reaction mixture was poured into an ice-water mixture, stirred for 1 hour, and then diluted with 500 mL of $CHCl_3$ to give a total volume of 1000 mL. The aqueous layer was extracted with $CHCl_3$ (2×100 mL). The combined organic extracts were washed with dilute sulfuric acid (200 mL), aqueous saturated sodium bicarbonate (2×200 mL) and water until neutral, dried over $MgSO_4$, and evaporated to dryness. The residue was dissolved in $CHCl_3$ (200 mL) and filtered through a 9.0 cm in diameter and 4 cm thick bed of silica gel, washed with $CHCl_3$ (2×100 mL) and filtrate was evaporated to dryness to afford crude 1-O-methyl-2-deoxy-4-thio-3,5-di-O-p-toluoyl-α,β-D-ribofuranose (formula 2) as a dark brown solid (24 g) which was dissolved in a acetolysis mixture containing acetic anhydride (200 mL), glacial acetic acid (200 mL), and conc. sulfuric acid (2.5 mL) and warmed to 40° C. for 1 hour, then was decomposed by the addition of anhydrous sodium acetate. The resulting mixture was partitioned between 500 mL of water and 300 mL of $CHCl_3$. The aqueous phase was extracted with $CHCl_3$ (2×100 mL). The combined $CHCl_3$ layers were evaporated to dryness in vacuo, then several portions of methanol were added and removed in vacuo to eliminate the last traces of acetic anhydride. The residue was purified by a flash column containing 100 g of silica gel and eluted with 6:1 cyclohexane-ethylacetate and appropriate fractions were combined and evaporated to give a white solid, which was crystallized by 95% ethanol to give 1-O-acetyl-2-deoxy-4-thio-3,5-di-O-p-toluoyl-α,β-D-ribofuranose, yield 18.26 g (70% from 1-O-methyl-2-deoxy-4-thio-α,β-D-ribofuranose) as a α,β mixture; MS z/e 429 $(M+1)^+$; $^1H$ NMR ($CDCl_3$, 300 MHz) $\delta 2.02$ (s, 3H, $CH_3CO$), 2.04 (s, 3H, $CH_3CO$), 2.34 (s, 6H, $CH_3$ of toluoyl), 2.36 (s, 6H, $CH_3$ of toluoyl), 2.52–2.74 (m, 4H, H-2), 3.92–4.06 (m, 2H, H-4), 4.28–4.52 (m, 4H, $CH_2$), 5.64–5.74 (m, 2H, H-3), 6.12 (dd, 1H, H-1 of β, J=3.0 and 6.0 Hz), 6.20 (d, 1H, H-1 of α, J=5.5 Hz), 7.24–7.36 (m, 4H, meta CH's of toluoyl), 7.8–7.92 (m, 4H, ortho CH's of toluoyl). Anal. Calcd. for $C_{23}H_{24}O_6S$: C, 64.47; H, 5.64; S, 7.48. Found C, 64.5; H, 5.67; S, 7.40.

EXAMPLE 2

9-(2-Deoxy-4-thio-3,5-di-O-toluoyl-α,β-D-ribofuranosyl)-2,6-dichloropurine (formula 4)

To a solution of 1-O-acetyl-2-deoxy-4-thio-3,5-di-O-p-toluoyl-α,β-D-ribofuranose (formula 3) (411 mg, 0.96 mmol) and 2,6-dichloropurine (181.5 mg, 0.96 mmol) in $CH_3CN$ (30 mL) was added Tin(IV) chloride (0.499 mg, 1.92 mmol) at 0° C. After the mixture was stirred for 1.5 hours, the reaction was essentially complete as indicated by TLC (cyclohexane-ethylacetate 3:1). The reaction mixture was concentrated to a small volume (about 5 mL), sodium bicarbonate (500 mg) and distilled water (2 mL) were added. When the vigorous evolution of carbon dioxide had ceased, the mixture was evaporated down under reduced pressure. The residue was dissolved in $CHCl_3$ (25 mL) and washed with water (2×15 mL), dried ($MgSO_4$), and evaporated to dryness. The residue contained one major and one minor component on TLC, and applied to a flash column containing 75 g of silica gel with cyclohexane-ethylacetate 5:1 to afford 9-(2'-deoxy-4'-thio-3',5'-di-O-toluoyl-α,β-D-ribofuranosyl)-2,6-dichloropurine (382 mg, 71%), mp 70°–71° C., TLC 3:1 cyclohexane-ethylacetate, $R_f$ 0.48; MS z/e 558 $(M+1)^+$; $^1H$ NMR ($CDCl_3$, 300 MHz) $\delta 2.40$ (s, 3, $CH_3$), 2.42 (s, 3, $CH_3$), 3.0 (br d, 2, H-2'), 4.38 (m, 1, H-4'), 4.52 (m, 2, 2 × H-5'), 5.86 (s, 1, H-3'), 6.42 (t, 1, H-1', J=3 Hz), 7.22 (d, =2, H's of toluoyl, J=8 Hz), 7.28 (d, 2, H's of toluoyl, J=8 Hz), 7.56 (d, 2, H's of toluoyl, J=8 Hz), 7.98 (d, 2, H's of toluoyl, J=8 Hz), 8.26 (s, 1, H-8); $^{13}C$ NMR ($CDCl_3$, 300 MHz) $\delta 21.68$, 21.71 ($CH_3$'s of toluoyl), 42.28 (C-2'), 54.66 (C-4'), 62.01 (C-1'), 64.82 (C-5'), 78.53 (C-3'), 125.71, 126.49, 129.26, 129.36, 129.42, 129.74 (toluoyl ring carbon), 131.49 (C-5), 144.25, 144.74 (toluoyl ring carbon), 145.58 (C-8), 151.71 (C-6), 152.57 (C-4), 152.89 (C-2), 165.37, 166.07 (carbonyl carbon of toluoyl).

EXAMPLE 3

9-(2-Deoxy-4-thio-α-D-ribofuranosyl)-2-chloro-6-aminopurine (formula 5)

A mixture of 9-(2-deoxy-4-thio-3,5-di-O-toluoyl-α-D-ribofuranosyl)-2,6-dichloropurine (formula 4) (300 mg, 0.54 mmol) and saturated ethanolic $NH_3$ (50 mL) was heated at 50° C. in a glass lined stainless steel pressure vessel for 48 hours. The reaction mixture was evaporated to dryness to afford a syrup which was purified on two silica gel thick plates (Analtech, GF, 1000 μM) that were developed in 4:1 $CHCl_3$-MeOH. The product was eluted with hot EtOH and evaporated. The residue was crystallized from 45 mL of boiling EtOH to give pure 9-(2-deoxy-4-thio-α-D-ribofuranosyl)-2-chloro-6-aminopurine: yield 122 mg 75%; mp 204°–205° C.; TLC 4:1 $CHCl_3$-MeOH, $R_f$ 0.45; MS z/e 302 $(M+1)^+$; UV $\lambda_{max}$ pH 1 267 (11.7), pH 7 266 (12.7), pH 13 265 (12.7); $^1$H NMR ($Me_2SO$-$d_6$, 300 MHz) δ2.38–2.48 (m, 1, H-2'), 2.60–2.68 (m, 1, H -2'), 3.36–3.56 (m, 2, H-5'), 3.62–3.70 (m, 1, H-4'), 4.40–4.46 (m, 1, H-3'), 5.06 (t, 1, 5'-OH, J=5 Hz), 5.52 (d, 1, 3'-OH, J=4 Hz), 6.12 (dd, 1 , H-1', J=4 and 8 Hz), 7.78 (br s, 2,$NH_2$), 8.50 (s, 1, H-8); $^{13}$C NMR ($Me_2SO$-$d_6$, 300 MHz) δ42.39 (C-2'), 58.33 (C-1', J=160.5 Hz), 59.91 (C-4'), 63.54 (C-5'), 74.35 (C-3'), 117.55 (C-5), 140.79 (C-8), 150.02 (C-4), 152.65 (C-2), 156.52 (C-6). Anal. ($C_{10}H_{12}ClN_5O_2S$) C, H, N, S.

EXAMPLE 4

9-(2-Deoxy-4-thio-3,5-di-O-toluoyl-α-D-ribofuransoyl)-2,6-diazidopurine (formula 6)

To a solution of 9-(2-deoxy-4-thio-3,5-di-O-toluoyl-α-D-ribofuranosyl)-2,6-dichloropurine (formula 4) (200 mg, 0.36 mmol) in 25 mL of EtOH was added a solution of sodium azide (46.8 mg, 0.72 mmol) in distilled water (10 mL) and the mixture was refluxed. A TLC aliquot at 2 hours showed complete reaction. The solution was evaporated, and the residue was dissolved in $CHCl_3$ (25 mL) and washed with water (20 mL), dried ($MgSO_4$), and evaporated to dryness. The residue was crystallized from MeOH to give 9-(2-deoxy-4-thio-3,5-di-O-toluoyl-α-D-ribofuranosyl)-2,6-diazidopurine (199 mg, 97%); mp 88°–90° C.; TLC 3:1 cyclohexane-ethylacetate; $R_f$ 0.45; MS z/e 571 $(M+1)^+$; $^1$H NMR ($CDCl_3$, 300 MHz) δ2.40 (s, 3, $CH_3$ of toluoyl), 2.42 (s, 3, $CH_3$ of toluoyl), 2.98 (br d, 2, H-2'), 4.34–4.38 (m, 1, H-4'), 4.44–4.56 (m, 2, 2 H-5'), 5.84 (br d, 1, H-4'), 6.36 (t, 1, H-1', J=3 Hz), 7.20 (d, 2, H's of toluoyl, J=8 Hz), 7.28 (d, 2, H's of toluoyl, J=8 Hz), 7.62 (d, 2, H's of toluoyl, J=8 Hz), 7.98 (d, 2, H's of toluoyl, J=8 Hz), 8.52 (s, 1, H-8); $^{13}$C NMR ($CDCl_3$, 300 MHz) δ21.67, 21.70 ($CH_3$'s of toluoyl), 42.12 (C-2'), 54.40 (C-4'), 61.19 (C-1'), 64.89 (C-5'), 78.45 (C-3'), 121.96 (C-5), 125.90, 126.57, 129.24, 129.32, 129.53, 129.75 (toluoyl ring carbon), 143.20 (C-8), 144.18, 144.57 (toluoyl ring carbon), 153.46 (C-4), 153.70, 155.90 (C-2, C-6), 165.47, 166.10 (carbonyl carbon of toluoyl).

EXAMPLE 5

9-(2-Deoxy-4-thio-3,5-di-O-toluoyl-α-D-ribofuranosyl)-2,6-diaminopurine (formula 7).

To a solution of 9-(2-deoxy-4-thio-3,5-di-O-toluoyl-α-D-ribofuranosyl)-2,6-diazidopurine (formula 6) (175 mg, 0.31 mmol) in $CH_2Cl_2$ (2 mL) was added MeOH (20 mL) and Tin(II) chloride (188.6 mg, 1 mmol) and the mixture was stirred at 25° C. A TLC aliquot at 1.5 hours showed complete reaction. The solution was evaporated to dryness, the residue was dissolved in $CHCl_3$ (50 mL) and washed with water (20 mL), and aqueous sodium bicarbonate (20 mL), dried ($MgSO_4$) evaporated to dryness. The residue was purified by 35 g of silica gel with $CHCl_3$-MeOH 95:5 to afford 9-(2-deoxy-4-thio-3,5-di-O-toluoyl-α-D-ribofuranosyl)-2,6-aminopurine (146 mg, 92%), mp 118°–121° C.; TLC 93:7 $CHCl_3$-MeOH; $R_f$ 0.48; MS z/e 519 $(M+1)^+$; $^1$H NMR ($Me_2SO$-$d_6$, 300 MHz) δ2.34 (s, 3, $CH_3$), 2.36 (s, 3, $CH_3$), 2.0–3.06 (m, 2, H-2'), 4.34–4.52 (m, 3, H-4', 2 x H-5'), 5.75 (br d, 1, H-3'), 5.90 (s, 2, C-2,$NH_2$), 6.18 (dd, 1, H-1', J=3 and 7 Hz), 7.26 (d, 2, H's of toluoyl, J=8 Hz), 7.32 (d, 2, H's of toluoyl, J=8 Hz), 7.70 (d, 2, H's of toluoyl, J=8 Hz), 7.90 (d, 2, H's of toluoyl, J=8 Hz), 8.08 (s, 1, H-8); $^{13}$C NMR ($Me_2SO$-$d_6$, 300 MHz) δ21.08, 21.10 ($CH_3$'s of toluoyl), 40.17 (C-2'), 52.69 (C-4'), 58.53 (C-1'), 64.90 (C-5'), 77.94 (C-3'), 113.40 (C-5), 126.35, 126.51 (toluoyl ring carbon), 129.07, 129.19, 129.26 (toluoyl ring carbon), 135.66 (C-8), 143.71, 143.74 (toluoyl ring carbon), 151.46 (C-4), 156.08 (C-6), 160.12 (C-2), 164.88, 165.24 (carbonyl carbon of toluoyl).

EXAMPLE 6

9-(2-Deoxy-4-thio-α-D-ribofuranosyl)-2,6-diaminopurine (formula 8)

A solution of 9-(2-deoxy-4-thio-3,5-di-O-toluoyl-α-D-ribofuranosyl)-2,6-diaminopurine (formula 7) (125 mg, 0.24 mmol) in anhydrous MeOH (25 mL) was stirred at room temperature with a freshly prepared solution of sodium methoxide (26 mg, 0.48 mmol) in MeOH (5 mL). A TLC aliquot at 1 hour showed complete reaction. The solution was rendered neutral with Dowex 50W-X8 ($H^+$) ion-exchange resin, the suspension was filtered, and the resin was washed with MeOH. The filtrates were combined and evaporated to dryness, and methyl p-toluate was removed at 50° C./0.01 torr. Crystallization of the residue from absolute EtOH gave pure 9-(2-deoxy-4-thio-α-D-ribofuranosyl)-2,6-diaminopurine, yield 63 mg (93%); mp 186°–188° C.; TLC 4:1 $CHCl_3$-MeOH, $R_f$ 0.30; MS z/e 283 $(M+1)^+$; UV $\lambda_{max}$ pH 1 292 (10.10) pH 7 280 (10.61), pH 13 280 (10.41); $^1$H NMR ($Me_2SO$-$d_6$, 300 MHz) δ2.30–2.40 (m, 1, H-2'), 2.54–2.68 (m, 1, H-2'), 3.34–3.40 (m, 1, H-5'), 3.52–3.60 (m, 1, H-5'), 3.68–3.74 (m, 1, H-4'), 4.48 (br t, 1, H-3'), 5.02 (t, 1, 5'-OH, J=6 Hz), 5.62 (d, 1, 3'-OH, J=4 Hz), 5.78 (s, 2,$NH_2$), 6.02 (dd, 1, H-1', J=3.0 and 8 Hz), 6.68 (s, 1,$NH_2$), 8.10 (s, 1, H-8); $^{13}$C NMR ($Me_2SO$-$d_6$, 300 MHz) δ42.56 (C-2'), 57.10 (C-1'), 59.65 (C-4'), 63.67 (C-5'), 74.38 (C-3'), 112.80 (C-5), 136.65 (C-8), 151.18 (C-4), 155.91 (C-2), 159.91 (C-6). Anal. ($C_{10}H_{14}N_6O_2S$) C, H, N, S.

EXAMPLE 7

9-(2-Deoxy-4-thio-α-D-ribofuranosyl)-2-amino-1,6-dihydro-6-oxopurine (formula 9)

To a solution of 9-(2-deoxy-4-thio-α-D-ribofuranosyl)-2,6-diaminopurine (formula 8) (30 mg, 0.11 mmol) in distilled $H_2O$ (10 mL) was added a suspension of adenosine deaminase in 3.2M $(NH_4)_2SO_4$ (0.1 mL) and reaction mixture was kept at room temperature. A 12-day TLC aliquot showed complete reaction. The solution was evaporated to dryness, the residue was crystallized from EtOH to give 9-(2-deoxy-4-thio-α-D-ribofuranosyl)-2-amino-1,6-dihydro-6-oxopurine (28 mg, 93%); mp 257°–260° C.; TLC 3: 1 $CHCl_3$, MeOH, $R_f$ 0.55; MS z/e 284 (M+1)$^+$, UV $\lambda_{max}$ pH 1 254 (11.15), pH 7 254 (12.51), pH 13 267 (11.09); $^1$H NMR (Me$_2$SO-d$_6$, 300 MHz) δ2.30–2.40 (m, 1, H-2'), 2.52–2.62 (m, 1, H-2'), 3.30–3.40 (m, 1, H-5'), 3.46–3.58 (m, 1, H-5'), 3.60–3.66 (m, 1, H-4'), 4.46 (br t, 1, H-3'), 5.04 (br t, 1, 5'-OH), 5.50 (d, 1, 3'-OH, J=4 Hz), 5.94 (dd, 1, H-1', J=4 and 8 Hz), 6.50 (s, 2,NH$_2$), 8.08 (s, 1, H-8); $^{13}$C NMR (Me$_2$SO-d$_6$, 300 MHz) δ42.57 (C-2'), 57.32 (C-1'), 59.63 (C-4'), 63.58 (C-5'), 74.34 (C-3'), 116.09 (C-5), 136.53 (C-8), 150.63 (C-4), 153.41 (C-2), 156.54 (C-6). Anal. (C$_{10}$H$_{13}$N$_5$O$_3$S) C, H, N, S.

EXAMPLE 8

9-(2-Deoxy-4-thio-3,5-di-O-toluoyl-α-D-ribofuranosyl)-2-fluoro-6-aminopurine (formula 10)

To a solution of 1-O-acetyl-2-deoxy-4-thio-3,5-di-O-p-toluoyl-α,β-D-ribofuranose (formula 3) (214 mg, 0.5 mmol) and 2-fluoroadenine (76.5 mg, 0.5 mmol) in CH$_3$CN (25 mL) was added Tin(IV) chloride (260 mg, 1.0 mmol) at 0° C. After the mixture was stirred for 1 hour, the reaction was almost complete as indicated by TLC (CHCl$_3$-MeOH 95:5). The reaction mixture was concentrated to a small volume (about 5 mL), sodium bicarbonate (300 mg) and distilled water (2 mL) were added. When the vigorous evolution of carbon dioxide had ceased, the mixture was evaporated under reduced pressure. The residue was dissolved in CHCl$_3$ (25 mL) and washed with water (2×10 mL), dried (MgSO$_4$), and evaporated to dryness. The residue contained one major and one minor component on TLC, and applied to a flash column containing 60 g of silica gel with CHCl$_3$-MeOH 98:2, to afford 9-(2-deoxy-4-thio-3,5-di-O-toluoyl-α-D-ribofuranosyl)-2-fluoro-6-aminopurine (200 mg, 76%); TLC CHCl$_3$-MeOH 95:5; $R_f$ 0.45; MS z/e 522 (M+1)$^+$; $^1$H NMR (CDCl$_3$, 300 MHz) δ2.45 (s, 3, CH$_3$ of toluoyl), 2.52 (s, 3, CH$_3$ of toluoyl), 2.98–3.0 (m, 2, H-2'), 4.34–4.40 (m, 1, H-4'), 4.45–4.58 (m, 2, H-5'), 5.82 (br s, 1, H-3'), 6.34 (dd, 1, H-1', J=3 and 5 Hz), 6.42 (br s, 2, NH$_2$), 7.16 (d, 2, H's of toluoyl, J=8 Hz), 7.26 (d, 2, H's of toluoyl, J=8 Hz), 7.60 (d, 2, H's of toluoyl), 7.96 (d, 2, H's of toluoyl), 8.38 (s, 1, H-8); $^{13}$C NMR (CDCl$_3$, 300 MHz) δ21.66, 21.70 (CH$_3$'s of toluoyl), 42.28 (C-2'), 54.38 (C-4'), 61.08 (C-1'), 64.97 (C-5'), 78.57 (C-3'), 118.30 (C-5, $J_{C-5,2-F}$=3.9 Hz), 126,09, 126.63, 129.23, 12 9.59, 129.76 (toluoyl ring carbon), 140.41 (C-8), 144.13, 144.43 (toluoyl ring carbon), 151.2 (C-4, $J_{C-4,2-F}$=19.7 Hz), 157.0 (C-6, $J_{C-6,2-F}$=20 Hz), 159 (C-2, $J_{C-2,2-F}$=211.3 Hz), 165.46, 166.11 (carbonyl carbon of toluoyl).

EXAMPLE 9

9-(2-Deoxy-4-thio-α-D-ribofuranosyl)-2-fluoro-6-aminopurine (formula 11)

A mixture of 9-(2-deoxy-4-thio-3,5-di-O-toluoyl-α-D-ribofuranosyl)-2-fluoro-6-aminopurine (formula 10) (175 mg, 0.33 mmol), and saturated ethanolic NH$_3$ (50 mL) was heated at 50° C. in a glass lined stainless steel pressure vessel for 48 hours. The reaction mixture was evaporated to dryness to afford a syrup which was purified on a silica gel thick plate (Analtech GF, 1000 μM) that were developed in 4:1 CHCl$_3$-MeOH. The product was eluted with hot EtOH and evaporated. The residue was crystallized from boiling EtOH to give pure 9-(2-deoxy-4-thio-α-D-ribofuranosyl)-2-fluoro-6-aminopurine (77.5 mg, 81%); mp 248°–250° C.; TLC 4:1 CHCl$_3$-MeOH, $R_f$ 0.48; MS z/e 286 (M+1)$^+$, UV $\lambda_{max}$pH 1 265 (11.7), pH 7 262 (13.5), pH 13 262 (13.5); $^1$H NMR (Me$_2$SO-d$_6$, 300 MHz) δ2.40–2.48 (m, 1, H-2'), 2.56–2.68 (m, 1, H-2'), 3.38–3.46 (m, t, H-5'), 3.48–3.58 (m, 1, H-5'), 3.62–3.70 (m, 1, H-4'), 4.42 (br t, 1, H-3', J=4 Hz), 5.06 (t, 1, 5'-OH, J=6 Hz), 5.52 (d, 1, 3'-OH, J=4 Hz), 6.08 (dd, 1, H-1', J=4 and 8 Hz), 7.70 (br s, 2, NH$_2$), 8.46 (s, 1, H-8); $^{13}$C NMR (Me$_2$SO-d$_6$, 300 MHz) δ42.35 (C-2'), 58.23 (C-4'), 59.82 (C-4'), 63.54 (C-5'), 74.37 (C-3'), 116.9 (C-5, $J_{C-5,2-F}$=4.2 Hz), 140.6 (C-8, $J_{C-8,2-F}$=2.0 Hz), 150.3 (C-4, $J_{C-4,2-F}$=20.3 Hz), 157.36 (C-6, $J_{C-6,2-F}$=21.2 Hz), 158.33 (C-2, $J_{C-2,2-F}$=203.5 Hz). Anal. (C$_{10}$H$_{12}$FN$_5$O$_2$S) C, H, N, S.

EXAMPLE 10

9-(2-Deoxy-4-thio-3,5-di-O-p-toluoyl-α,β-D-ribofuranose-6-chloropurine (formula 12)

To a solution of 1-O-acetyl-2-deoxy-4-thio-3,5-di-O-p-toluoyl-α,β-D-ribofuranose (formula 3) (428 mg, 1.0 mmol) and 6-chloropurine (154.5 mg, 1.0 mmol) in CH$_3$CN (40 mL) was added Tin(IV) chloride (0.521 mg, 2 mmol) at 0° C. After the mixture was stirred for 2 hours, the reaction was essentially complete as indicated by TLC (CHCl$_3$-MeOH 98:2). The reaction mixture was concentrated to a small volume (about 5 mL), sodium bicarbonate (500 mg), and distilled water (2 mL) were added. When the vigorous evolution of carbon dioxide had ceased, the mixture was evaporated under reduced pressure. The residue was dissolved in CHCl$_3$ (30 mL) and washed with water (2×20 mL), dried (MgSO$_4$), and evaporated to dryness. The residue contained one major and one minor component on TLC, and applied to a flash column containing 75 g of silica gel with CHCl$_3$-MeOH 99:1 to afford pure 9-(2-deoxy-4-thio-3,5-di-O-toluoyl-α,β-D-ribofuranosyl)-6-chloropurine (365.5 mg, 70%); TLC 97:3 CHCl$_3$-MeOH $R_f$ 0.60; MS z/e 523 (M+1)$^+$; $^1$H NMR (CDCl$_3$, 300 MHz) δ2.92–3.02 (m, 1, H-2'), 3.04–3.12 (m, 1, H-2'), 4.36–4.54 (m, 1, H-4'), 4.50–4.58 (m, 2, H-5'), 5.85 (br t, 1, H-3', J=3.0 Hz), 6.48 (dd, 1, H-1', J=2 and 5.0 Hz), 7.20 (d, 2, H's of toluoyl, J=8 Hz), 7.26 (d, 2, H's of toluoyl, J=8 Hz), 7.56 (d, 2, H's of toluoyl, J=8 Hz), 7.98 (d, 2, H's of toluoyl, J=8 Hz), 8.76 (s, 1, H-2 or H-8), 8.78 (s, 1, H-2 or H-8); $^{13}$C NMR (CDCl$_3$, 300 MHz) δ21.68, 21.71 (CH$_3$'s of toluoyl), 42.04 (C-2'), 54.58 (C-4'), 61.71 (C-1'), 64.87 (C-3'), 78.43 (C-5'), 125.76, 126.54, 129.25, 129.34, 129.76, 129.44 (toluoyl ring carbon), 132.43 (C-5), 146.20, 144.66 (toluoyl ring carbon), 144.83 (C-8, $^1J_{C-8,H-8}$=215 Hz, $^3J_{C-8,H-1}$=3.6 Hz), 151.04 (C-6, $^3J_{C_6H_2}$=13.7 Hz), 151.36 (C-4, $^3J_{C-4,H_8}$=12.1 Hz, $^3J_{C_4,H-4}$=4.5 Hz), 151.84 (C-2, $^1J_{C-2,H-2}$=209.6 Hz), 165.43, 166.09 (carbonyl carbon of toluoyl).

EXAMPLE 11

9-(2-Deoxy-4-thio-α-D-ribofuranosyl-6-aminopurine (formula 13)

A mixture of 9-(2'-deoxy-4'-thio-3',5'-di-)-toluoyl-α-D-ribofuranosyl)-6-chloropurine (formula 12) (340 mg, 0.65 mmol) and saturated ethanolic NH$_3$ (50 mL) was heated at 50 ° C. in a glass-lined stainless steel pressure vessel for 3 days. The reaction mixture was evaporated to dryness to afford a syrup which was purified on three silica gel thick plates (Analtech, GF, 1000 μM), that were developed in 4:1 CHCl$_3$-MeOH. The product was eluted with hot EtOH and evaporated. The residue was crystallized from boiling EtOH to give pure 9-(2-deoxy-4-thio-α-D-ribofuranosyl)-6-aminopurine (148 mg, 85%); mp 218°–220° C.; TLC 4:1 CHCl$_3$-MeOH, $R_f$ 0.30; MS z/e 268 (M+1)$^+$, UV $\lambda_{max}$ pH 1 260 (14.7), pH 7 261 (15.2), pH 13 261 (15.3); $^1$H NMR (Me₂SO-d₆, 300 MHz) δ2.40–2.52 (m, 1, H-2'), 2.60–2.70 (m, 1, H-2'), 3.36–3.44 (m, 1, H-5'), 3.50–3.58 (m, 1, H-5'), 3.64–3.70 (m, 1, H-4'), 4.38–4.46 (m, 1, H-3'), 5.06 (t, 1, 5'-OH, J=4.5 Hz), 5.64 (d, 1, 3'-OH, J=4 Hz), 6.20 (dd, 1, H-1', J=4 and 7.5 Hz), 7.26 (s, 2,NH₂), 8.15 (s, 1, H-2), 8.50 (S, 1, H-8 ); ¹³H NMR (Me₂SO-d₆, 300 MHz) δ42.42 (C-2'), 58.03 (C-1'), 59.85 (C-4'), 63.60 (C-5'), 74.47 (C-3'), 118.59 (C-5), 140.20 (C-8), 148.96 (C-4), 152.14 (C-2), 155.78 (C-6). Anal. (C₁₀H₁₃N₅O₂S) C, H, N, S.

EXAMPLE 12

9-(2-Deoxy-4-thio-α-D-ribofuranosyl)-1,6-dihydro-6-oxypurine (formula 14)

To a solution of 9-(2-deoxy-4-thio-α-D-ribofuranosyl)-6-aminopurine (formula 13) (50 mg, 0.18 mmol) in distilled H₂O (10 mL) was added a suspension of adenosine deaminase in 3.2M (NH₄)₂SO₄ (0.2 mL) and the reaction mixture was kept at room temperature. A TLC aliquot at 18 hours showed complete reaction. The solution was evaporated to dryness. The residue was crystallized from hot EtOH to give 9-(2'-deoxy-4'-thio-α-D-ribofuranosyl)-1,6-dihydro-6-oxopurine (40 mg, 80%); mp 198°–200° C.; TLC 3:1 CHCl₃-MeOH, R_f 0.50; MS z/e 269 (M+1)⁺; UV λ_max pH 1 251 (11.76), pH 7 251 (12.45), pH 13 255 (13.68); ¹H NMR (Me₂SO-d₆, 300 MHz) δ2.41–2.50 (m, 1, H-2'), 2.60–2.70 (m, 1, H-2'), 3.4 6–3.44 (m, 1, H-5'), 3.48–3.58 (m, 1, H-5'), 3.64–3.72 (m, 1, H-4'), 4.44 (dd, 1, H-3', J=2 and 7 Hz), 6.18 (dd, 1, H-1', J=3 and 8 Hz), 8.06 (s, 1, H-8), 8.66 (s, 1, H-2) ¹³C NMR (Me₂SO-d₆, 300 MHz) δ42.53 (C-2'), 58.44 (C-1', $J_{C,H}$=160.59 Hz), 59.87 (C-4, $J_{C,H}$=161.26 Hz) 63.42 (C-5), 74.40 (C-3'), 123.78 (C-5), 139.58 (C-8, $J_{C_8,H_8}$=215.3 Hz, $J_{C_8,H-1}$=4.7 Hz), 145.68 (C-2, $J_{C,H}$=205.5 Hz), 167.81 (C-6), 156.50 (C-4).

EXAMPLE 13

1-(2-Deoxy-4-thio-3,5-di-O-toluoyl-β-D-ribofuranosyl)uracil (formula β-15) and 1-(2-deoxy-4-thio-3,5-di-O-toluoyl-α-D-ribofuranosyl)uracil (formula α-15)

To a suspension of 1-O-acetyl-2-deoxy-4-thio-3,5-di-O-p-toluoyl-α,β-D-ribofuranose (formula 3) (428 mg, 1.0 mmol) and uracil(2,4-dioxopyrimidine) (112.1 mg, 1.0 mmol) in anhydrous acetonitrile (30 mL) were added consecutively hexamethyldisilazane (HMDS, 161.5 mg, 1.0 mmol) and trimethylchlorosilane (TMSCl, 108.6 mg, 1.0 mmol) and the mixture was stirred at room temperature. After 0.5 hours, the resulting solution was cooled to –78° C. and trimethylsilyl trifluoromethanesulfonate (266.7 mg, 1.2 mmol) was added to it and stirred at the same temperature for another 1 hour, after which time the reaction was essentially complete. The reaction mixture was warmed to room temperature and concentrated to a small volume (5 mL), diluted with methylene chloride (about 50 mL), then washed with water (15 mL) followed by saturated sodium bicarbonate and finally with water. The organic layer was dried over MgSO₄ and evaporated to dryness. The residue was purified by 50 g of silica gel with CHCl₃-MeOH 98:2 to afford a solid, which was crystallized from CHCl₃-dioxane to give pure 1-(2-deoxy-4-thio-3,5-di-O-toluoyl-β-D-ribofuranosyl)uracil (185 mg, 38%); mp 182°–184° C.; TLC 98:2 CHCl₃-MeOH; R_f 0.35; MS z/e 481 (M+1)⁺; ¹H NMR (CDCl₃, 300 MHz) δ2.42 (s, 6H, CH₃ of toluoyl), 2.36–2.44 (m, 1H, H-2'), 2.70–2.80 (m, 1H, H-2'), 3.96–4.02 (m, 1H, H-4'), 4.56–4.62 (m, 2H, H-5'), 5.66–5.70 (m, 1H, H-5), 5.72–5.76 (m, 1H, H-3'), 6.60 (t, 1H, H-1', J=8.0 Hz), 7.26 (d, 4H, H's of toluoyl, J=8 Hz), 7.80 (d, 1H, H-6), 7.90–7.96 (m, 4H, H's of toluoyl), 8.86 (s, 1H, H-3). ¹³C NMR (CDCl₃, 300 MHz), δ21.732 (CH₃ of toluoyl), 40.152 (C-2'), 52.903 (C-4'), 61.328 (C-1'), 64.822 (C-5'), 76.797 (C-3'), 103. 499 (C-5'), 126.283, 126.458, 129.171, 129.704, 129.766, 129. 837 (toluoyl ring carbons), 140.005 (C-6), 144.415, 144.493 (toluoyl ring carbon), 150.401 (C-2), 162.387 (C-4), 165.574, 166.140 (carbonyl carbon of toluoyl). Fractional crystallization of mother liquor from EtOH-dioxane afforded 1-(2-deoxy-4-thio-3,5-di-O-toluoyl-α-D-ribofuranosyl)uracil (192 mg, 40%); mp 118°–120° C.; TLC 98:2 CHCl₃-MeOH; R_f 0.35; MS z/e 481 (M+1)⁺; ¹H NMR (CDCl₃, 300 MHz) ∊2.40 (s, 6H, CH₃ of toluoyl), 2.54–2.60 (m, 1H, H-2'), 2.84–2.96 (m, 1, H-2'), 4.20–4.26 (m, 1H, H-4'), 4.38–4.52 (m, 2H, H-5'), 5.68–5.72 (m, 2H, H-3', H-5) 6.44 (brd, 1H, H-6, J= 12 Hz), 7.26 (d, 4H, H's of toluoyl, J=8 Hz), 7.30 (d, 2H, H's of toluoyl, J=8 Hz), 7.96 (d, 2H, H's of toluoyl, J=8 Hz), 8.14 (d, 2H, H-6, J=8 Hz), 9.48 (s, 1H, H-3); ¹³C NMR (CDCl₃, 300 MHz) δ21.718 (CH₃ of toluoyl), 42.148 (C-2'), 54.46 (C-4'), 63.55 (C-1'), 64.96 (C-5'), 78.21 (C-3'), 101.94 (C-5), 126.03, 126.55, 129.23, 129.27, 129.73, 129.63 (toluoyl ring carbon), 141.74 (C-6), 144.14, 144.73 (toluoyl ring carbon), 150.71 (C-2), 163.05 (C-4), 165.36, 166.07 (carbonyl carbon of toluoyl).

EXAMPLE 14

2'-Deoxy-4'-thiouridine (formula β-16) and 1-(2-Deoxy-4-thio-α-D-ribofuranosyl)uracil (formula α-16)

A solution of 1-(2-deoxy-4-thio-3,5-di-O-toluoyl-β-D-ribofuranosyl)uracil (formula 15) (175 mg, 0.36 mmol) in anhydrous MeOH (30 mL) was stirred at room temperature with a freshly prepared solution of sodium methoxide (39 mg, 0.72 mmol) in MeOH (6.5 mL). A TLC aliquot at 2.5 hours showed complete reaction (CHCl₃-MeOH, 95:5). The solution was rendered neutral with Dowex 50W-X8 (H⁺) ion-exchange resin, the suspension filtered, and the resin was washed with MeOH. The filtrate was combined and evaporated to dryness, and methyl p-toluate was removed at 50° C./0.01 torr. Crystallization of the residue from absolute EtOH gave pure 2'-deoxy-4'-thiouridine (76 mg, 85%); mp 186°–88° C.; TLC 9:1 CHCl₃-MeOH, R_f 0.30; MS z/e 245 (M+1)⁺, UV λ_max pH 1 266 (9.88), pH 7 266 (9.76), pH 13 266 (8.08); ¹H NMR (DMSO-d₆, 300 MHz) δ2.10–2.22 (m, 2H, H-2'), 3.20–3.34 (m, 1H, H-4'), 3.52–3.62 (m, 2H, H-5'), 4.36 (s, 1H, H-3'), 5.18 (br s, 1H, OH), 5.30 (br s, 1H, OH), 5.68 (d, 1H, H-5, J=8 Hz), 6.26 (t, 1H, H-1', J=7.0 Hz), 8.0 (d, 1H, H-6, J=8 Hz), 11.34 (br s, 1H, H-3). ¹³C NMR (DMSO-d6, 300 MHz) δ41.246 (C-2'), 58.981 (C-4'), 60.108 (C-1'), 63.465 (C-5'), 73.438 (C-3'), 102.133 (C-5, J=175.92 Hz), 141.354 (C-6, J=180.75 Hz), 150.615 (C-2), 162.743 (C-4). Anal. Calcd. for C₉H₁₂N₂O₄S: C, 44.25; H, 4.95;N, 11.46; S, 13.12. Found: C, 44.20; H, 4.97; N, 11.42; S, 13.03. 1-(2-deoxy-4-thio-3,5-di-O-toluoyl-α-D-ribofuranosyl)uracil was deprotected in a similar manner as described for 2'-deoxy-4'-thiouridine to provide pure 1-(2-deoxy-4-thio-α-D-ribofuranosyl)uracil (75 mg, 85%), mp 190°–192° C.; TLC 9:1 CHCl₃-MeOH, R_f 0.30; MS z/e 245 (M+1)⁺, UV λ_max pH 1 266 (9.24), pH 7 266 (9.52), pH 13 265 (8.72); ¹H NMR (Me₂SO-d₆, 300 MHz) δ2.0–2.28 (m, 1, H-2'), 2.44–2.54 (m, 1H, H-2'), 3.30–3.38 (m, 1H, H-5'), 3.40–3.48 (m, 1H, H-5'), 3.50–3.56 (m, 1H, H-4'), 4.32 (br dd, 1, H-3', J=2 and 8 Hz), 5.64 (d, 1H, H-6, J=8 Hz), 6.14 (dd, 1, H-1', J=3 and 7.5 Hz), 8.26 (d, 1H, H-5, J=8 Hz); ¹³C NMR (Me$_2$SO-d$_6$, 300 MHz) δ42.16 (C-2), 60.01 (C-4'), 60.95 (C-1'), 63.57 (C-5'), 74.14 (C-3') 101.16 (C-5, J$_{C,H}$=175.24 Hz), 142.92 (C-6, J$_{C,H}$=181.88 Hz), 150.69 (C-2), 162.97 (C-4). Anal. Calcd. for C$_9$H$_{12}$N$_2$O$_4$S: C, 44.25; H, 4.95; N, 11.46; S, 13.12. Found: C, 44.17; H, 4.97; N, 11.39; S, 13.21.

EXAMPLE 15

3',5'-Di-O-toluoyl-4'-thiothymidine (formula β-17) and 1-(2-Deoxy-4-thio-3,5-di-O-toluoyl-α-D-ribofuranoyl)thymine (formula α-17)

To a suspension of 1-O-acetyl-2-deoxy-4-thio-3,5-di-O-p-toluoyl-α,β-D-ribofuranose (formula 3) (428 mg, 1.0 mmol), and thymine(5-methyl-2,4-dioxopyrimidine) (126 mg, 1.0 mmol) in anhydrous acetonitrile (30 mL) were added consecutively hexamethyldisilazane (HMDS, 161.5 mg, 1.0 mol), and trimethylchlorosilane (TMSCl, 108.6 mg, 1.0 mmol), and the mixture was stirred at room temperature after 0.5 hours. The resulting solution was cooled to −78° C. and trimethylsilyl trifluoromethanesulfonate (266.7 mg, 1.2 mmol) was added to it and stirred at the same temperature for another 1.5 hours, after which time the reaction was essentially complete. The reaction mixture was warmed to room temperature and concentrated to a small volume (5 mL), diluted with methylene chloride (about 50 mL), then washed with water (15 mL) followed by saturated sodium bicarbonate and finally with water. The organic layer was dried over MgSO$_4$ and evaporated to dryness. The residue was purified by 50 g of silica gel with CHCl$_3$-MeOH 99:1 to afford a solid which was crystallized from EtOH-CHCl$_3$ to give pure 3',5'-di-O-toluoyl-4'-thiothymidine (173 mg, 35%); mp 178°–182° C.; TLC 98:2 CHCl$_3$-MeOH, R$_f$ 0.55; MS z/e 495 (M+1)$^+$; $^1$H NMR (CDCl, 300 MHz) δ1.78 (s 3H, C-5 CH$_3$ ), 2.42 (s, 3H, CH$_3$ of toluoyl), 2.43 (s, 3H, CH$_3$ of toluoyl), 2.36–2.44 (m, 1H, H-2'), 3.98–4.04 (m, 1H, H-4'), 4.12 (d, 2H, H-5', J=6 Hz), 5.76 (br t, 1H, H-3'), 6.66 (dd, 1H, H-1', J=6 and 9 Hz), 7.26 (d, 4H, H's of toluoyl, J=8 Hz), 7.56 (s, 1H, H-6), 7.94 (d, 2H, H's of toluoyl, J=8 Hz), 7.96 (d, 2H, H's of toluoyl, J=8 Hz), 8.58 (s, 1H, H-3); $^{13}$C NMR (CDCl$_3$, 300 MHz) δ12.41 (C-5, CH$_3$), 21.69, 21.72 (CH$_3$'s of toluoyl), 39.98 (C-2'), 53.13 (C-4', J$_{C,H}$=148.1 Hz), 61.27 (C-1', J$_{C,H}$=163.3 Hz) 65.14 (C-5'), 77.13 (C-3'), 112.28 (C-5), 126.41, 126.58 (toluoyl ring carbon), 129.23, 129.35, 129.74, 129.87 (toluoyl ring carbon), 135.46 (C-6, J$_{C,H}$=176.46 Hz), 144.38, 144.47 (toluoyl ring carbon), 150.45 (C-2), 162.90 (C-4), 165.61, 166.17 (carbonyl carbon of toluoyl).

Fractional crystallization of mother liquor from EtOH-dioxane afforded 1-(2-deoxy-4-thio-3,5-di-O-tolyoyl-α-D-ribofuranosyl)thymine (185 mg, 38%); mp 146°–148° C.; TLC 98:2 CHCl$_3$-MeOH; R$_f$ 0.55; MS z/e 495 (M+1)$^+$; $^1$H NMR (CDCl$_3$, 300 MHz) δ1.82 (s, 3H, C-5, CH$_3$), 2.40 (s, 6H, CH$_3$ of toluoyl), 2.50–2.58 (m, 1H, H-2'), 2.85–2.95 (m, 1H, H-2'), 4.22–4.30 (m, 1H, H-4'), 4.38–4.52 (m, 2H, H-5'), 5.70–5.74 (m, 1H, H-3'), 6.54–6.58 (dd, 1H, H-1', CK=4 and 2 Hz), 7.26 (d, 4H, H's of toluoyl, J=8 Hz), 7.80 (d, 2H, H's of toluoyl, J=8 Hz), 7.86 (s, 1H, H-6), 7.96 (d, 2H, H's of toluoyl, J=8 Hz), 8.82 (s, 1H, H-3); $^{13}$C NMR (CDCl$_3$, 300 MHz) δ12.667 (C-5 CH$_3$), 21.707 (CH$_3$ of toluoyl), 42.046 (C-2'), 54.392 (C-4'), 62.971 (C-1', J$_{C,H}$=161.0 Hz) 65.054 (C-5'), 78.235 (toluoyl ring carbon), 110.473 (C-5), 126.183, 126.590 (toluoyl ring carbon), 129.227, 129.308, 129.569, 129.744 (toluoyl ring carbons), 137.254 (C-6), 144.144, 144.643 (toluoyl ring carbon), 150.600 (C-2), 163.350 (C-4), 165.395, 166.114 (carbonyl carbon of toluoyl).

EXAMPLE 16

4'-Thiothymidine (formula α-18) and 1-(2-deoxy-4-thio-α-D-ribofuranosyl)thiamine (formula β-18)

A solution of 3',5'-di-O-toluoyl-4'-thiothymidine (formula β-17) (150 mg, 0.30 mmol) in anhydrous MeOH (30 mL) was stirred at room temperature with a freshly prepared solution of sodium methoxide (32.5 mg, 0.60 mmol) in MeOH (7.5 mL). A TLC aliquot at 3 hours showed complete consumption of starting material (TLC CHCl$_3$-MeOH 95:5). The solution was rendered neutral with Dowex 50W-X8 (H$^+$) ion-exchange resin, the suspension was filtered, and the resin was washed with MeOH. The filtrates were combined and evaporated to dryness, and methyl p-toluate was removed at 50° C./0.01 torr. Crystallization of the residue from absolute EtOH gave pure 4'-thiothymidine (61 mg, 78%), mp 213°–215° C.; TLC 9:1 CHCl$_3$-MeOH, R$_f$=0.40; MS z/e 258 (M+1)$^+$, UV λ$_{max}$ pH 1 272 (10.3), pH 7 272 (10.2), pH 13 271 (10.3 ); $^1$H NMR (Me$_2$SO-d$_6$, 300 MHz) δ1.80 (S, 3H, C-5, CH$_3$), 2.10–2.24 (m, 2H, H-2'), 3.24–3.32 (m, 1H, H-4'), 3.50–3.66 (m, 2H, H-5'), 4.38 (br s, 1H, H-3'), 5.16 (br t, 1H, 5'-OH), 5.24 (d, 1H, 3'-OH, J=4 Hz), 6.30 (dd, 1, H-1', J=6.5 and 8 Hz), 7.32 (s, 1H, H-6), 11.32 (br s, 1H, H-3); $^{13}$C NMR (Me$_2$SO-d$_6$, 300 MHz) δ12.14 (C-5, CH$_3$) 40.93 (C-1', J$_{C,H}$=132.33 Hz), 59.01 (C-4', J$_{C,H}$=143.3 Hz), 59.93 (C-1', J$_{C,H}$=161.74), 63.51 (C-5'), 73.40 (C-3') 109.82 (C-5), 136.70 (C-6, J$_{C,H}$=179 Hz), 150.59 (C-4) 163.37 (C-2) Anal Calcd. for C$_{10}$H$_{13}$N$_2$O$_4$S: C, 46.68; H, 5.09;N, 10.88; S, 12.46. Found: C, 46.59 H, 5.56; N, 10.74; S, 12.18.

1-(2-deoxy-4-thio-3,5-di-O-toluoyl-α-D-ribofuranosyl)thymine was deprotected in a similar manner as described for 3',5'-di-O-toluoyl-4'-thiothymidine to provide 1-(2-deoxy-4'-thio-α-D-ribofuranosyl)thymine, mp 205°–207° C.; TLC 9:1 HCl$_3$-MeOH, R$_f$ 0.40; MS z/e 258 (M+1)$^+$, UV λ$_{max}$ pH 1 271 (10.5), pH 7 271 (10.5), pH 13 271 (8.64); $^1$H NMR (DMSO-d$_6$, 300 MHz) δ1.80 (s, 3H, C-5, CH$_3$), 2.0–2.10 (m, 1H, C-2'), 2.46–2.54 (m, 1H, H-2'), 3.36–3.44 (m, 1H, H-5'), 3.54–3.60 (m, 2H, H-5', H-4'), 4.26 (br d, 1H, H-3', J=2 Hz), 5.0 (br s, 1H, 5'-OH), 5.48 (br s, 1H, 3'-OH), 36.16 (dd, 1H, H-1', J=4 and 2 Hz), 8.10 (s, 1H, H-6), 11.24 (br s, 1H, H-3), $^{13}$C NMR (DMSO-d$_6$, 300 MHz) δ12.260 (C-5, CH$_3$), 42.027 (C-2'), 59.533 (C-4'), 59.772 (C-1', J$_{C,H}$=168.0 Hz), 63.574 (C-5'), 74.05 (C-3'), 108.944 (C-5), 138.285 (C-6, J$_{C,H}$=179.61 Hz), 150.285 (C-2), 163.467 (C-4). Anal. Calcd. for C$_{10}$H$_{13}$N$_2$O$_4$S: C, 46.68; H, 5.09; N, 10.88; S, 12.46. Found: C, 46.60 H, 5.54;N, 10.81; S, 12.22.

EXAMPLE 17

1-(2-Deoxy-4-thio-3,5-di-O-toluoyl-α,β-D-ribofuranosyl)cytosine (formula 19)

To a suspension of 1-O-acetyl-2-deoxy-4-thio-3,5-di-O-p-toluoyl-α,β-D-ribofuranose (formula 3) (428 mg, 1.0 mmol) and cytosine (111.1 mg, 1.0 mmol) in anhydrous acetonitrile (25 mL) were added consecutively hexamethyl disilazane (HMDS, 161.6 mg, 1.0 mmol) and trimethylchloro silane (TMSCl, 108.6 mg, 1.0 mmol), and the mixture was stirred at room temperature for 0.5 hours. The resulting solution was cooled to −78° C. and trimethylsilyl trifluoromethanesulfonate (266.7 mg, 1.2 mmol) was added to it and stirred at the same temperature for another 2.5 hours after which time the reaction was essentially complete. The reaction mixture was warmed to room temperature and concentrated to a small volume (5 mL), diluted with methylene chloride (50 mL), then washed with water (20 mL) followed by saturated sodium bicarbonate and finally with water. The organic layer was dried over $MgSO_4$ and evaporated to dryness. The residue was purified by 50 g of silica gel with $CHCl_3$-MeOH (98:2) to afford a solid which was passed through a 15 cm bed of silica gel to afford 1-(2'-deoxy-4'-thio-3',5'-di-O-toluoyl-α,β-D-ribofuranosyl)cytosine (397 mg 80%) as colorless syrup TLC $CHCl_3$-MeOH (90:10), $R_f$ 0.45; MS z/e 480 (M+1)$^+$, $^1$H NMR (CDCl$_3$, 300 MHz) δ2.36 (s, 6H, CH$_3$of toluoyl), 2.40 (s, 6H, CH$_3$ of toluoyl), 2.36–2.42 (m, 1H, H-2'), 2.58–2.64 (m, 1H, H-2'), 2.70–2.76 (m, 1H, H-2'), 2.80–2.90 (m, 1H, H-2'), 3.94–4.0 (m, 1H, H-4'), 4.15–4.24 (m, 1H, H-4'), 4.36–4.50 (m, 2H, H-5'), 4.50–4.56 (m, 2H, H-5'), 5.66–5.68 (m, 1H, H-3'), 5.70–5.74 (m, 1H, H-3'), 5.76 (d, 1H, H-6, J=8 Hz), 5.86 (d, 1H, H-6, J=8 Hz), 6.48 (dd, 1H, H-1'α, J=4 and 2 Hz), 6.70 (brt, 1H, H-1'β, J=8 Hz), 7.17–7.28 (m, 8 H, H's of toluoyl), 7.76 (d, 1H, H-6, J=8 Hz), 7.84–7.96 (m, 8H, H's of toluoyl), 8.16 (d, 1H, H-6, J=8 Hz); $^{13}$C NMR (DMSO-d$_6$, 300 MHz), δ21.696 (CH$_3$of toluoyl), 40.169 (C-2'β), 42.150 (C-2'α), 52.404 (C-4'β), 54.218 (C-4'α), 62.179 (C-1'β), 64.410 (C-1'α), 65.163 (C-5'), 65.373 (C-5'), 76.934 (C-3'), 78.418 (C-3'), 94.199 (C-4), 95.757 (C-4), 126.305, 126.471, 126.603, 126.686, 129.099, 129.186, 129.746, 129.835, 141.471, 143.075, 144.022, 144.196, 144.294, 144, 331, 156.076, 156.261, 165.401, 165.431, 165.631, 165.666, 166.153, 166.213.

EXAMPLE 18

1-(2-Deoxy-4-thio-α,β-D-ribofuranoslyl)cystosine (formula 20)

A solution of 1-(2-deoxy-4-thio-3',5-di-O-toluoyl-α,β-D-ribofuranosyl)cytosine (formula 19) (298 mg, 0.6 mmol) in anhydrous MeOH (50 mL) was stirred at room temperature with a freshly prepared solution of sodium methoxide (65 mg, 1.2 mmol), in MeOH (10 mL). A 2.5 hour TLC aliquot showed complete consumption for starting material [TLC CHCl$_3$-MeOH (80:20)]. The solution was neutralized with Dowex 50W-X8 (H$^+$) ion-exchange resin, the suspension was filtered and the resin was washed with MeOH. The filtrates were combined and evaporated to dryness and methyl p-toluate was removed at 50° C./0.01 torr. Residue failed to crystallize and was passed through a 3-cm bed of silica gel to obtain 1-(2'-deoxy-4'-thio-α,β-D-ribofuranosyl)cytosine as amorphous solid; $^1$H NMR (DMSO-d$_6$, 300 MHz) δ1.90–2.04 (m, 1H, H-2'α), 2.06–2.16 (m, 2H, H-2'β), 2.40–2.48 (m, 1H, H-2'α), 3.20–3.40 (m, 2H, H-5'), 3.40–3.50 (m, 6H, H-5', H-4') 4.26 (m 1 H H-3') 4.36 (m, 1H, H-3'), 5.0 (m, 1H, 5'-OH), 5.12 (m, 1H, 5'-OH), 5.22 (br d, 1H, 3'-OH), 5.42 (br d, 1H, 3'-OH), 5.74 (d, 1H, H-5, J=8 Hz), 5.78 (d, 1H, H-5, J=8 Hz), 6.20 (dd, 1H, H-1'α, J=4 and 2 Hz), 6.34 (t, 1H, H-1'β, J=8 Hz), 7.12 (br t, 4H, NH$_2$), 7.94 (d, 1H, H-6, J=8 Hz), 8.18 (d, 1H, H-6, J=8 Hz).

EXAMPLE 19

2'-Deoxy-4'-thiocytidine (formula β-20)

To a solution of 1-(2-deoxy-4-thio-3,5-di-O-toluoyl-β-D-ribofuranosyl)uracil (formula β-15) (240 mg, 0.5 mmol) in 50 mL of pyridine was added 1,2,4-triazole (1.0 mmol), and p-chlorophenyl-phosphodichloridate (0.75 mmol) and the reaction mixture was stirred at room temperature for 3 days during which time starting material was almost completely consumed. The reaction mixture was evaporated to a syrup under reduced pressure which was then passed through a funnel having a 3-cm layer of silica gel to afford crude 1-(2-deoxy-4-thio-3,5-di-O-toluoyl-β-D-ribofuranosyl)-4-(1,2,4-triazol-1-yl)-2-pyrimidinone (formula 21) (300 mg); MS z/e 532 (M+1)$^+$ which was treated with conc. NH$_4$OH dioxane (25 mL, 1:1) for 12 hours at room temperature. Evaporation of solvent and subsequent treatment of the residue with 2 eq. of NaOMe in MeOH (30 mL) for 2 hours afforded crude 2'-deoxy-4'-thiocytidine (formula β-20) which was crystallized from ethanol as an amorphous powder (75 mg, 62%) 129°–132° C. (hydroscopic); MS z/e 244 (M+1)$^+$; $^1$H NMR (DMSO-d$_6$, 300 MHz) δ2.04–2.16 (m, 2H, H-2'), 3.26–3.30 (m, 1H, H-5'), 3.40–3.58 (m, 2H, H-5', H-4') 5.16 (t 1H, 5'-OH, J=5 Hz), 5.24 (d, 1H, 3'-OH, J-4 Hz), 5.68 (d, 1H, H-5, J=8 Hz), 6.36 (brt, 1H, H-1', J=7.5 Hz), 7.10–7.24 (m, 2H, NH$_2$), 7.94 (d, 1H, H-6, J=8 Hz); $^{13}$C NMR (DMSO-d$_6$, 300 MHz) δ41.638 (C-2'), 58.627, 60.356 (C-4', C-1') 63.666 (C-3') 94.528 (C-5) 141.896 (C-6), 155.239 (C-4), 165.039 (C-2). Anal. Calcd. for $C_9H_{13}N_3O_3S$: C, 44.44; H, 5.38;N, 17.27; S, 13.18. Found C, 44.37 H, 5.42; N, 17.19; S, 13.09.

EXAMPLE 20

Antiviral activity of 2'-deoxy-4'-thioribonucleosides

2'-Deoxy-4'-thioribonucleosides were tested for antiviral activity against viruses that replicate in mammalian cells growing in cell culture. The results of these tests against herpes simplex virus, Type 1 and Type 2, are summarized in Table 1. The Virus Rating (VR) is a standard weighted measurement of antiviral activity which takes into account the degree of inhibition of virus-induced cytopathogenic effects (CPE) and the degree of Cytotoxicity produced by the test compound, determined by a modification of the method of Ehrlich et al, Ann. N.Y. Acad. Sci. 130, 5–16 (1965).

The CPE-inhibition assays were designed to test seven 0.5 $log_{10}$ concentrations of each compound, beginning with 320 µg/mL, against HSV in triplicate 24-hour Vero cell monolayers in 96-well tissue culture plates. To each of the replicate cell cultures were dispensed 0.1 mL of the test compound solution (or suspension) and 0.1 mL of HSV suspension (diluted in medium to yield 32 CCID$_{50}$ units per 0.1 mL). Cell controls, untreated virus-infected controls and drug cytotoxicity controls were included in each assay. The plates were incubated at 37° C. in a humidified atmosphere containing 2% CO$_2$ until 100% CPE were observed in the untreated virus control cultures. The cell monolayers were examined microscopically for drug cytotoxicity and for CPE which was graded on a scale of 0–4 (0–100% CPE).

The VR was calculated as 0.1 of the sum of the numerical differences between the recorded CPE grade of each test well and that of the corresponding virus control in the culture plate. Numerical differences between the scores of test wells containing a drug concentration which is partially cytotoxic and their corresponding virus controls were halved.

In tests carried out by this method, a greater value of VR indicates greater antiviral activity. A compound with a VR of 1.0 or greater is considered to have significant antiviral activity with a high degree of reproducibility in confirmatory in vitro tests. A compound with a VR of 0.5–0.9 is considered to have possible or marginal activity; a compound with a VR of less than 0.5 is considered to be inactive.

The MIC$_{50}$ (minimum inhibitory concentration, 50%) is the concentration of a test compound required for 50% inhibition of virus-induced cytopathogenic effect calculated by using a regression analysis program for semilog curve fitting. MTC (minimum toxic concentration) is the minimum drug concentration (µg/ml) causing any cytotoxicity. TI is the therapeutic index, calculated by dividing the minimum cytotoxic drug concentration (MTC) by the minimum inhibitory concentration, 50% (MIC$_{50}$). The results were compared with two commercial antiviral agents, acyclovir and 9-β-D-arabinofuranosyladenine (Ara-A). The tests summarized in Table I show that definite antiviral activity against herpes simplex Type 1 is exhibited by two of the invention compounds, 4' thiothymidine and 1-(2-deoxy-4-thio-α-D-ribofuranosyl)thymine.

TABLE 1

| Compound | Virus | VR | MIC$_{50}$ (mg/ml) | MIC (mg/ml) | TI |
|---|---|---|---|---|---|
| 9-(2-Deoxy-4-thio-α-D-ribofuranosyl)-2-chloro-6-aminopurine | HSV-1[a] | 0 | | | |
| | HSV-2[b] | 0 | | | |
| 9-(2-Deoxy-4-thio-α-D-ribofuranosyl)-2-fluoro-6-aminopurine | HSV-1 | 0 | | | |
| | HSV-2 | 0 | | | |
| 9-(2-Deoxy-4-thio-α-D-ribofuranosyl)-6-aminopurine | HSV-1 | 0 | | | |
| | HSV-2 | 0 | | | |
| 1-(2-Deoxy-4-thio-α-D-ribofuranosyl)-thymine | HSV-1 | 1.4 | 110.1 | >257.2 | 2.3 |
| | HSV-2 | 0.3 | — | >257.3 | — |
| 4'-thiothymidine | HSV-1 | 1.3 | 0.8 | 2.6 | 3.2 |
| | HSV-2 | 0.1 | — | 2.6 | — |
| 9-(2-Deoxy-4-thio-α-D-ribofuranosyl)-2,6-diaminopurine | HSV-1 | 0 | | | |
| | HSV-2 | 0 | | | |
| Controls | | | | | |
| Acyclovir | HSV-1 | 6.7 | 0.5 | >225.2 | >441 |
| | HSV-2 | 4.8 | 3.6 | >225.2 | 63.2 |
| Ara-A | HSV-1 | 1.8 | 15.2 | 84.8 | 5.6 |
| | HSV-2 | 1.1 | 39.3 | 84.8 | 2.2 |

[a]HSV-1 (E377)
[b]HSV-2 (MS)

EXAMPLE 21

Activity of 4'-thiothymidine against HCMV

4'-Thiothymidine was tested against human cytomegalovirus (HCMV) in MRL5 cell monolayer cultures.

MRC5 cells were infected with HCMV to give a multiplicity of infection of about 0.05 Plaque-forming units/cell. Aliquots of drug solution were introduced into the cell cultures 1.5 hours later (2 virus-infected cultures and one uninfected control). A week post infection the cells were examined microscopically for cytopathogenic effects and drug cytotoxicity. Drug toxicity was determined quantitatively by a method based on the reduction of the tetrazolium salt MTT. The infectious virus yields from the harvested test and virus control samples were determined by plaque assay in MRC5 cells grown in 12-well cluster plates. Inhibition of HCMV replication by the test compounds was determined by comparing the progeny virus yields in the drug-treated cultures with the progeny virus yields in the untreated, virus-infected controls. Ganciclovir, (9-[[2-hydroxy-1-(hydroxymethyl)ethoxy]methyl]guanine), a known antiviral agent, was tested as a positive control. The tests summarized in Table 2 show that the activity of 4'-thiothymidine was comparable to that of ganciclovir, although 4'-thiothymidine was more toxic to MRC5 cells.

TABLE 2

| | Drug Cytotoxicity | | | |
|---|---|---|---|---|
| Conc. (μM) | HCMV Yield[a] | Yield Reduction[a] | Gross Morphology | MTT Assay (Percent of Control) |
| 4'-thiothymidine | | | | |
| 100 | 1.1 | 3.8 | sl. toxic | 86 |
| 32 | 1.8 | 3.1 | sl. toxic | 81 |
| 10 | 3.6 | 1.3 | 0 | 90 |
| 3.2 | 4.1 | 0.8 | 0 | 81 |
| 1.0 | 4.4 | 0.5 | — | — |

TABLE 2-continued

| | Drug Cytotoxicity | | | |
|---|---|---|---|---|
| Conc. (μM) | HCMV Yield[a] | Yield Reduction[a] | Gross Morphology | MTT Assay (Percent of Control) |
| untreated, virus-infected control | | | | |
| 0 | 4.9 | — | | |
| ganciclovir | | | | |
| 32 | 1.3 | 3.6 | 0 | 95 |

[a]log$_{10}$ Plaque-forming units/ml

EXAMPLE 22

Antitumor activity of 2'-deoxy-4'-thioribonucleosides

2'-Deoxy-4'-thioribonucleosides were tested for antitumor activity against leukemia L1210 ("L1210") cells and human epidermoid carcinoma No. 2 ("H.Ep.-2") cells.

Table 3 sets forth the results of cytotoxicity tests. For L1210 cells the IC$_{50}$ is the concentration required to decrease cellular proliferation by 50% as compared to untreated controls. The cells were grown in suspension cultures and the number of cells present was determined at 24 and 48 hours. The values shown in Table 2 are 48 hour values.

For H.Ep.-2 cells, the IC$_{50}$ is the concentration required to reduce colony formation by 50% as compared to controls. One hundred cells in 10 mL of medium were placed in prescription bottles, and after 10 days incubation, the medium was decanted and the colonies were stained and counted.

In the cytotoxicity tests, the lower the IC$_{50}$ value, the greater the antitumor activity. An IC$_{50}$ value of less than 40 μg/mL indicates a compound of interest, and an IC$_{50}$ value of less than 1 indicates a compound that is extremely effective. As shown in Table 2 below, all the compounds tested show an IC$_{50}$ value of less than 40 μg/mL with respect to either H.Ep.-2 or L1210 cells, or both.

TABLE 3

| Compound | IC$_{50}$ (μg/mL) | |
|---|---|---|
| | H.Ep.-2 | L1210 |
| 9-(2-Deoxy-4-thio-α-D-ribofuranosyl)-2-chloro-6-aminopurine | 20 | >40 |
| 9-(2-Deoxy-4-thio-α-D-ribofuranosyl)-6-aminopurine | 30 | >40 |
| 9-(2-Deoxy-4-thio-α-D-ribofuranosyl)-2-fluoro-6-aminopurine | >40 | 30 |

EXAMPLE 23

Antitumor activity of 2'-deoxy-4'-thioribonucleosides (cont.)

Certain 2'-deoxy-4'-thioribopyrimidines were tested for antitumor activity against murine leukemia L1210, Human Epidermoid Carcinoma #2 and Human T-cell leukemia CCRF-CEM according to the method set forth in J. A. Secrist, A. T. Shortnacy and J. A. Montgomery, *J. Med. Chem.* 1988, 31, 405. The results, summarized in Table 4 show that 4'-thiothymidine is the most cytotoxic of these thionucleosides to all three neoplastic cell lines, although 2'-deoxy-4'-thiocytidine and 2'-deoxy-4'-thiouridine are also quite cytotoxic.

TABLE 4

| Compound | IC$_{50}$ (μg/mL) | | |
|---|---|---|---|
| | L1210 | H.Ep.-2 | CCRF—CEM |
| 1-(2-Deoxy-4-thio-α, β-D-ribofuranosyl)cytosine | 0.82 | 0.20 | 3.5 |
| 2'-Deoxy-4'-thiocytidine | 1.3 | 0.20 | — |
| 2'-Deoxy-4'-thiouridine | 2.7 | 2.1 | >4 |
| 2'-Thiothymidine | 0.12 | 0.055 | 0.66 |
| 4'-(2-Deoxy-4-thio-α-D-ribofuranosyl)uracil | I[a] | I[a] | — |
| 1-(2-Deoxy-4-thio-α-D-ribofuranosyl)thymine | 66 | 36 | — |

[a]No cytotoxicity at 160 μM, the highest level tested.

EXAMPLE 24

The procedures of Examples 13–19 are followed except that one of the following pyrimidine, 5-azapyrimidine, 6-azapyrimidine, or 3-deazapyrimidine bases are used in place of uracil, thymine or cytosine to form the corresponding 2'-deoxy-4'-thioribonucleosides: 5-halo-substituted uracil, 5-halo-substituted cytosine, 5-methyl cytosine, 5-azauracil, 5-azacytosine, 6-azauracil, 6-azathymine, 6-aza-5-halo-substituted uracil, 6-azacytosine, 6-aza-5-methyl cytosine, 6-aza-5-halo-substituted cytosine, 3-deazauracil, 3-deazathymine, 3-deaza-5-halo substituted uracil, 3-deazacytosine, 3-deaza-5-methyl cytosine, or 3-deaza-5-halo-substituted cytosine.

Although the invention has been described in considerable detail with specific reference to certain advantageous embodiments thereof, variations and modifications can be made without departing from the scope of the invention as described in the specification and defined in the appended claims.

We claim:
1. A compound having the formula

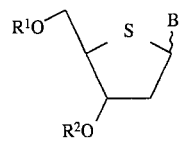

wherein B is selected from the group consisting of

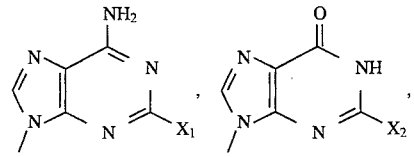

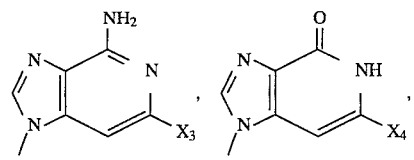

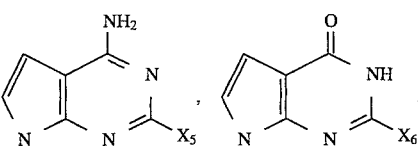

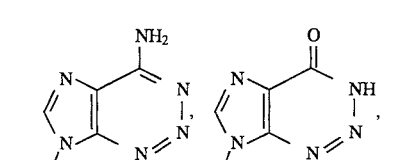

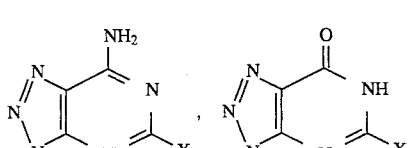

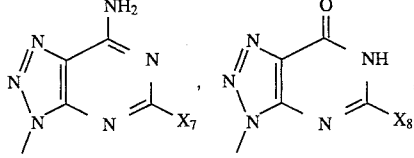

wherein $X_{1-8}$ are selected from the group consisting of hydrogen, $NH_2$ and halogen; wherein $X_9$ is selected from the group of hydrogen, methyl; and $X_{10}$ is selected from the group consisting of hydrogen, methyl and halogen; and wherein $R^1$ and $R^2$ are selected from the group of hydrogen, acyl protecting groups, and mixtures thereof.

2. A compound according to claim 1 wherein $R^1$ and $R^2$ are hydrogen.

3. A compound according to claim 1 wherein $R^1$ and $R^2$ are hydrogen.

4. A compound according to claim 1 which is 9-(2-deoxy-4-thio-α-D-ribofuranosyl)-2-chloro-6-aminopurine.

5. A compound according to claim 1 which is 9-(2-deoxy-4-thio-α-D-ribofuranosyl)-2,6-diaminopurine.

6. A compound according to claim 1 which is 9-(2-deoxy-4-thio-α-D-ribofuranosyl)-2-amino-1,6-dihydro-6-oxopurine.

7. A compound according to claim 1 which is 9-(2-deoxy-4-thio-α-D-ribofuranosyl)-2-fluoro-6-aminopurine.

8. A compound according to claim 1 which is 9-(2-deoxy-4-thio-α-D-ribofuranosyl)-6-aminopurine.

9. A compound according to claim 1 which is 9-(2-deoxy-4-thio-α-D-ribofuranosyl)-1,6-dihydro-6-oxopurine.

10. A compound according to claim 1 which is 1-(2-deoxy-4-thio-α-D-ribofuranosyl)uracil.

11. A compound according to claim 1 which is 2'-deoxy-4'-thiouridine.

12. A compound according to claim 1 which is 4'-thiothymidine.

13. A compound according to claim 1 which is 1-(2-deoxy-4-thio-α-D-ribofuranosyl)thymine.

14. A compound according to claim 1 which is 1-(2-deoxy-4-thio-α,β-D-ribofuranosyl)cytosine.

15. A compound according to claim 1 which is 2'-deoxy-4'-thiocytidine.

16. A compound having the formula

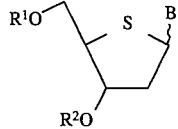

wherein B is a member selected from the group consisting of:

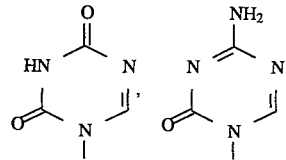

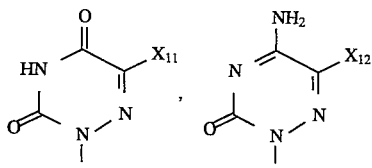

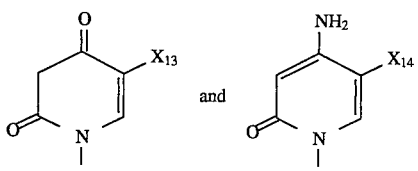

wherein $X_{11-14}$ are selected from the group of H, CH3, and halogen, and $R^1$ and $R^2$ is selected from the group of hydrogen, acyl protecting groups, and mixtures thereof.

17. A compound having the formula

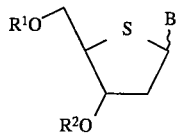

wherein B is selected from the group consisting of pyrimidine and purine nucleoside bases with the provision that when B is pyrimidine, B is not a uracil molecule having a halogen at the $C^5$-heterocyclic carbon of the molecule; and wherein $R^1$ and $R^2$ are selected from the group consisting of hydrogen, acyl protecting groups, and mixtures thereof.

18. A method for producing an antiviral effect against a virus that replicates in a virus-infected mammalian cell which method comprises contacting said cell with a compound according to the formula

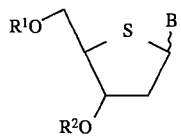

wherein B is selected from the group consisting of

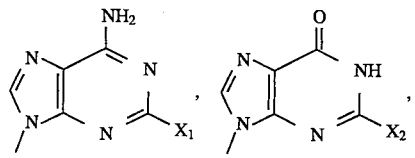

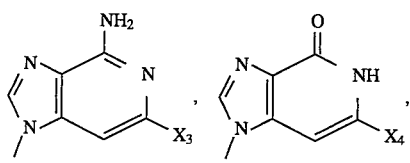

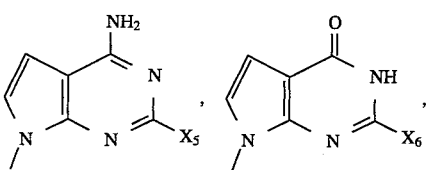

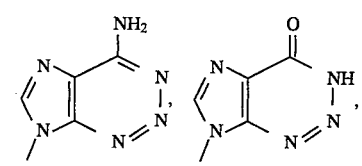

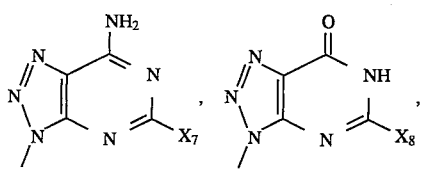

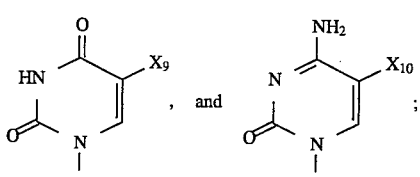

wherein $X_{1-8}$ are selected from the group consisting of hydrogen, $NH_2$ and halogen; wherein $X_9$ is selected from the group consisting of hydrogen, methyl; wherein $X_{10}$ is selected from the group consisting of hydrogen, methyl and halogen; and wherein $R^1$ and $R^2$ are selected from the group of hydrogen, acyl protecting groups, and mixtures thereof; said virus being herpes simplex virus or human cytomegalovirus.

19. A method according to claim 18 wherein the virus is a herpes simplex virus.

20. A method according to claim 18 wherein the antiviral effect is the inhibition of cytopathogenic effects produced by herpes simplex virus type 1, and wherein the compound is selected from the group consisting of 4'-thiothymidine and 1-(2-deoxy-4-thio-62-D-ribofuranosyl)thymine.

21. A method according to claim 18 wherein the antiviral effect is the inhibition of cytopathogenic effects produced by the human cytomegalovirus, and wherein the compound is 4'-thiothymidine.

* * * * *